United States Patent
Cole et al.

(10) Patent No.: US 6,221,074 B1
(45) Date of Patent: Apr. 24, 2001

(54) FEMORAL INTRAMEDULLARY ROD SYSTEM

(75) Inventors: J. Dean Cole; Carl A. Knobloch, both of Orlando, FL (US)

(73) Assignee: Orthodyne, Inc., Orlando, FL (US)

( * ) Notice: Subject to any disclaimer, the term of this patent is extended or adjusted under 35 U.S.C. 154(b) by 0 days.

(21) Appl. No.: 09/329,688

(22) Filed: Jun. 10, 1999

(51) Int. Cl.⁷ .............................. A61B 17/72; A61B 17/78
(52) U.S. Cl. .............................. 606/62; 606/64; 606/67; 606/60
(58) Field of Search ................ 606/60, 62, 64, 606/67

(56) References Cited

U.S. PATENT DOCUMENTS

| | | | |
|---|---|---|---|
| D. 341,884 | 11/1993 | Cohen et al. | D24/133 |
| 2,136,471 | 11/1938 | Schneider | 128/92 |
| 2,406,987 | 9/1946 | Anderson | 128/85 |
| 2,672,861 | 3/1954 | Jonas et al. | 128/92 |
| 2,675,801 | 4/1954 | Bambara et al. | 128/92 |
| 2,821,979 | 2/1958 | Cameron | 128/92 |
| 2,947,308 | 8/1960 | Gorman | 128/92 |
| 3,459,180 | 8/1969 | Ross | 128/92 |
| 3,561,437 | 2/1971 | Orlich | 128/92 |
| 3,893,196 | 7/1975 | Hochman | 128/92 |
| 4,261,351 | 4/1981 | Scherfel | 128/92 |
| 4,404,693 | 9/1983 | Zweymuller | 128/92 |
| 4,438,762 | 3/1984 | Kyle | 128/92 |
| 4,457,301 | 7/1984 | Walker | 128/92 |
| 4,475,545 * | 10/1984 | Ender | 128/92 |
| 4,697,585 * | 10/1987 | Williams | 128/92 |
| 4,776,330 * | 10/1988 | Chapman et al. | 606/62 |
| 4,827,917 * | 5/1989 | Brumfield | 606/62 |
| 4,846,162 | 7/1989 | Moehring | 128/92 |
| 4,858,602 * | 8/1989 | Seidel et al. | 128/92 |
| 4,875,474 * | 10/1989 | Border | 128/92 |
| 4,946,459 * | 8/1990 | Bradshaw et al. | 606/62 |
| 4,978,349 * | 12/1990 | Frigg | 606/67 |
| 4,993,410 * | 2/1991 | Kimsey | 606/100 |
| 5,032,125 * | 7/1991 | Durham et al. | 606/62 |
| 5,034,013 * | 7/1991 | Kyle et al. | 606/62 |
| 5,041,114 * | 8/1991 | Chapman et al. | 606/62 |
| 5,053,035 * | 10/1991 | McLaren | 606/67 |
| 5,066,296 * | 11/1991 | Chapman et al. | 606/64 |
| 5,100,404 * | 3/1992 | Hayes | 606/64 |

(List continued on next page.)

FOREIGN PATENT DOCUMENTS

| | | | |
|---|---|---|---|
| 0118778 * | 2/1984 | (EP) | 606/64 |
| 0551588 * | 2/1984 | (EP) | 606/64 |
| 3928460 * | 2/1984 | (DE) | 606/64 |
| 0565812 * | 10/1993 | (EP) | 606/64 |

OTHER PUBLICATIONS

Vector Intertrochantoric Nail Surgical Technique, Biomet Inc., All 1998.*

Vector® Intertrochanteric Nail Surgical Technique, Biomet, Inc., P.O. Box 587, Warsaw, IN 46581–0587, (219) 267–6639 © 1998 Biomet, Inc. Form No. Y–BMT–578/073198/K.

Primary Examiner—Paul J. Hirsch
Assistant Examiner—Michael B. Priddy
(74) Attorney, Agent, or Firm—Woodard, Emhardt, Naughton, Moriarty & McNett

(57) ABSTRACT

A femoral intramedullary rod system capable of treating a variety of femoral bone fractures using a uniform intramedullary rod design. The system generally comprising an intramedullary rod defining an opening having an upper surface and a transverse member including a bone engaging portion and a connection portion defining a thru-hole with the nail sized to pass therethrough. A pin is selectively coupled to the transverse member to rigidly assemble the transverse member to the nail when the nail is passed through the thru-hole and the pin is received within the opening.

26 Claims, 15 Drawing Sheets

U.S. PATENT DOCUMENTS

| | | | |
|---|---|---|---|
| 5,122,141 | * | 6/1992 | Simpson et al. .................. 606/62 |
| 5,176,681 | * | 1/1993 | Lawes et al. .................... 606/64 |
| 5,190,544 | * | 3/1993 | Chapman et al. ................ 606/65 |
| 5,201,735 | * | 4/1993 | Chapman et al. ................ 606/67 |
| 5,263,955 | * | 11/1993 | Baumgart et al. ................ 606/63 |
| 5,300,074 | * | 4/1994 | Frigg .............................. 606/70 |
| 5,312,402 | * | 5/1994 | Schlapfer et al. ................ 606/53 |
| 5,364,398 | * | 11/1994 | Chapman et al. ................ 606/69 |
| 5,484,439 | * | 1/1996 | Olson et al. .................... 606/65 |
| 5,549,610 | * | 8/1996 | Russell et al. .................. 606/64 |
| 5,562,666 | * | 10/1996 | Brumfield ........................ 606/64 |
| 5,569,249 | * | 10/1996 | James et al. .................... 606/62 |
| 5,573,536 | * | 11/1996 | Grosse et al. .................... 606/60 |
| 5,578,035 | * | 11/1996 | Lin ................................. 606/68 |
| 5,653,709 | * | 8/1997 | Frigg .............................. 606/64 |
| 5,704,939 | * | 1/1998 | Justin ............................. 606/63 |
| 5,713,902 | * | 2/1998 | Friedl ............................. 606/64 |
| 5,743,908 | * | 4/1998 | Kim ................................ 606/64 |
| 5,749,872 | * | 5/1998 | Kyle et al. ...................... 606/69 |
| 5,766,174 | * | 6/1998 | Perry ............................. 606/62 |
| 5,855,579 | * | 1/1999 | James et al. .................... 606/62 |
| 5,928,235 | * | 9/1999 | Friedl ............................. 606/64 |
| 5,935,127 | * | 8/1999 | Border ............................ 606/62 |
| 6,019,761 | * | 2/2000 | Jonas et al. ..................... 128/92 |

* cited by examiner

FEMORAL INTRAMEDULLARY ROD SYSTEM

FIELD OF THE INVENTION

The present invention is directed to techniques for treating bone fractures. Specifically, but not exclusively, the invention relates to a system for treating a variety of typical femoral fractures using a uniform intramedullary rod design.

BACKGROUND OF THE INVENTION

The femur generally comprises an elongated shaft extending from the hip to the knee. The proximal end of the femoral shaft includes a neck segment connected to a head portion. The head portion fits into a concavity of the hip bone to form a ball and socket joint at the hip. The distal end of the femoral shaft engages the upper end of the tibia to form the knee joint. Overall, the femur is one of the longest and strongest bones in the human body; however, portions of the femur are extremely susceptible to fracture.

Internal fixation of femoral fractures is one of the most common orthopedic surgical procedures. Many different types of femoral fractures are encountered in practice, including fractures of the femoral neck, midshaft, and distal regions. When the femur is fractured, treatment requires that the fractured bone be substantially immobilized and held together in an abutting relationship during the healing process. Any longitudinal, transverse, or rotational movement of one section of the fractured bone relative to the other can cause substantial delay in healing time or cause improper healing to occur. In general, two different internal fixation approaches have been used to immobilize the area surrounding the fracture site.

One approach involves driving metallic pins through the two sections of bone to be joined and connecting them to one or more plates bearing against the external surface of the bones. However, such an arrangement injures the flesh and muscle surrounding the bones and a large number of pins driven through the bone tend to weaken its hard outer layer. Plates also tend to stress the bone and are not always able to bear sufficient stress for many femoral fracture applications.

Further, bone beneath the plate does not always become as strong as it would in the absence of the plate. A second approach to treating femoral fractures involves the use of an intramedullary nail which is inserted into the medullary canal of the femur and affixed therein by a number of different methods. After complete healing of the bone at the fracture site, the nail may be removed through a hole drilled in the proximal end of the femur. A wide variety of devices have been developed over the years for use in the internal fixation of femoral fractures utilizing the method of intramedullar stabilization and immobilization. While there have been a number of technological advances made within the area of intramedullary fixation of femoral fractures, several problem areas remain.

One such problem arises from the fact that most intramedullary fixation systems currently available are adapted to a specific type of femoral fracture, resulting in a large number of highly specialized configurations. This has led to the disadvantageous consequence that hospitals and trauma centers have to keep a large inventory of incremental nail lengths with varying configurations and ancillary parts in order to accommodate a random and diverse incoming patient population. Maintaining such a high level of inventory to handle all expected contingencies is not only complex, but is also very expensive. Correspondingly, the possibility of error during selection and implantation of the fixation device by the surgeon is elevated. Likewise, the inventory costs associated with varying methods of intramedullary fixation are drastically increased and, in the case of smaller medical facilities, may necessitate switching to a less costly and potentially less effective method of treating femoral fractures.

Another problem may result from intramedullary rod systems used to specifically treat fractures of the neck or head of the femur. These devices typically include a transverse fixation member (nail, pin, screw, etc.) adapted to be positioned along the longitudinal axis of the femoral neck with its leading end portion embedded in the femoral head so as to grip the femoral head and thereby stabilize the fracture site. The fixation member is operably connected to the intramedullary rod to maintain a fixed relationship between the fixation member and the rod. Unfortunately, this structural connection does not always prevent rotational or translational movement of the fixation member relative to the intramedullary rod in response to forces commonly resulting from the normal activity of a convalescing patient. Additionally, the intramedullary rods used in these devices are typically specialized for use with this single fixation application and can not be used in other applications. Therefore, the costs associated with maintaining increased levels of inventory are substantially increased. Furthermore, if it is desired to vary the angle of the fixation member relative to the rod, substantial modifications must typically be made to either the fixation member or the rod member to accommodate for such an angular variation, again driving up inventory levels and associated inventory costs.

In still another problem area, on occasion, it is necessary to use transverse locking bone screws to lock the rod into position relative to the femur. In order to prevent the screws from backing out, locking nuts can be threaded onto the distal ends of the locking screws. Unfortunately, the installation of locking nuts onto the ends of the locking screws requires additional surgical incisions and commonly causes soft tissue irritation.

In yet another problem area, when an intramedullary rod is inserted into the medullary canal and anchored to the femur by two or more bone screws, despite the best efforts of the surgeon, the fracture site may have either been over-compressed or over-distracted as a result of the insertion of the rod. Unfortunately, with conventional intramedullary rods, it is virtually impossible to adjust the amount of distraction or compression without first removing one or more of the bone screws and manually distracting or compressing the fracture site. The intramedullary rod must then be re-anchored to the femur by reinserting the bone screws at different positions along the femur.

Thus, there is a demand for bone treatment techniques to address these problems. The present invention meets this demand and provides other benefits and advantages in a novel and unobvious manner.

SUMMARY OF THE INVENTION

The present invention is directed to techniques for treating bone fractures. Various aspects of the invention are novel, nonobvious and provide various advantages. While the actual nature of the invention covered herein can only be determined with reference to the claims appended hereto, selected forms and features of the preferred embodiment as disclosed herein, are described briefly as follows.

One form of the present invention includes treating a bone fracture with a nail that defines an opening and a transverse member including a bone engaging portion and a connection portion. The connection portion defines a through-hole and the nail is sized to pass through the through-hole. A pin is adjustably coupled to the transverse member to rigidly assemble the transverse member to the nail.

In a further form of the present invention, a method of treating a bone fracture includes forming a first hole in a femur transverse to the medullary canal and introducing a transverse member through the first hole. The transverse member includes a through-hole that is positioned relative to the medullary canal of the femur, and is preferably aligned therewith. The method further includes forming a second hole intersecting the medullary canal and inserting an intramedullary nail into the medullary canal via the second hole. The nail passes through the through-hole of the transverse member. The nail may include an opening aligned with the transverse member to facilitate rigid assembly to the transverse member by positioning a pin coupled to the transverse member in the nail opening.

In still another form of the present invention, a system for treating bone fractures includes a nail having a first end portion opposite a second end portion along a longitudinal axis. The first end portion defines an opening extending through the nail and has an angled surface oriented at an oblique angle relative to the longitudinal axis of the nail. Also included is a sleeve that includes a pair of apertures positioned on opposite sides of the sleeve. The apertures and the opening align to form a passageway when the sleeve is fitted over an end portion. A bone engaging member is received within the passageway in an abutting relationship with the angled surface.

In yet another form of the present invention, a bone fracture treatment apparatus includes an elongated nail having a longitudinal axis and a transverse axis generally perpendicular to the longitudinal axis. The nail defines a transverse opening extending along the transverse axis with the opening being bound by an upper surface and an opposite lower surface. At least one of the upper or lower surface defines a projection extending in a longitudinal direction to thereby narrow a dimension of the opening within the nail. The nail opening, and projection may be arranged to cooperate with one or more other members suitable to treat a particular type of bone fracture, such as a fracture of the femur.

According to another form of the present invention, a system for treating bone fractures includes a nail defining a longitudinal axis, a transverse axis and an opening extending along the transverse axis with the opening being bound by a bearing surface. Also included is a sleeve having a pair of apertures positioned on opposite sides thereof. The apertures and the opening are aligned to form a passageway when the sleeve is fitted over the nail. A bone engaging member is sized to pass through the passageway. Additionally, the system may include a means for biasing the sleeve in a longitudinal direction to clamp the bone engaging member against the bearing surface.

Still a further form of the present invention includes a technique for treating bone fractures with a nail that defines a longitudinal axis, an elongated opening extending therethrough, and a longitudinal passage intersecting the opening. A bone engaging member passes through the opening and a positioning device is provided that may be adjusted to change position of the bone engaging member along the longitudinal axis relative to the nail when the member is positioned through the nail opening. This device may be utilized to facilitate compression or distraction of a bone fracture.

Accordingly, one object of the present invention is to provide an improved bone fracture treatment system. Preferably, this system may be used to treat fractures of the femur.

Additionally or alternatively, another object is to provide an improved method of treating bone fractures, particularly fractures of elongated bones such as the femur.

Additionally or alternatively, still another object is to reduce the complexity and inventory costs associated with treating bone fractures.

Other objects, features, forms, embodiments, aspects, advantages and benefits of the present invention will become apparent to persons of ordinary skill in the art from the following written description and accompanying figures.

DESCRIPTION OF THE PREFERRED EMBODIMENTS

Figure 1:
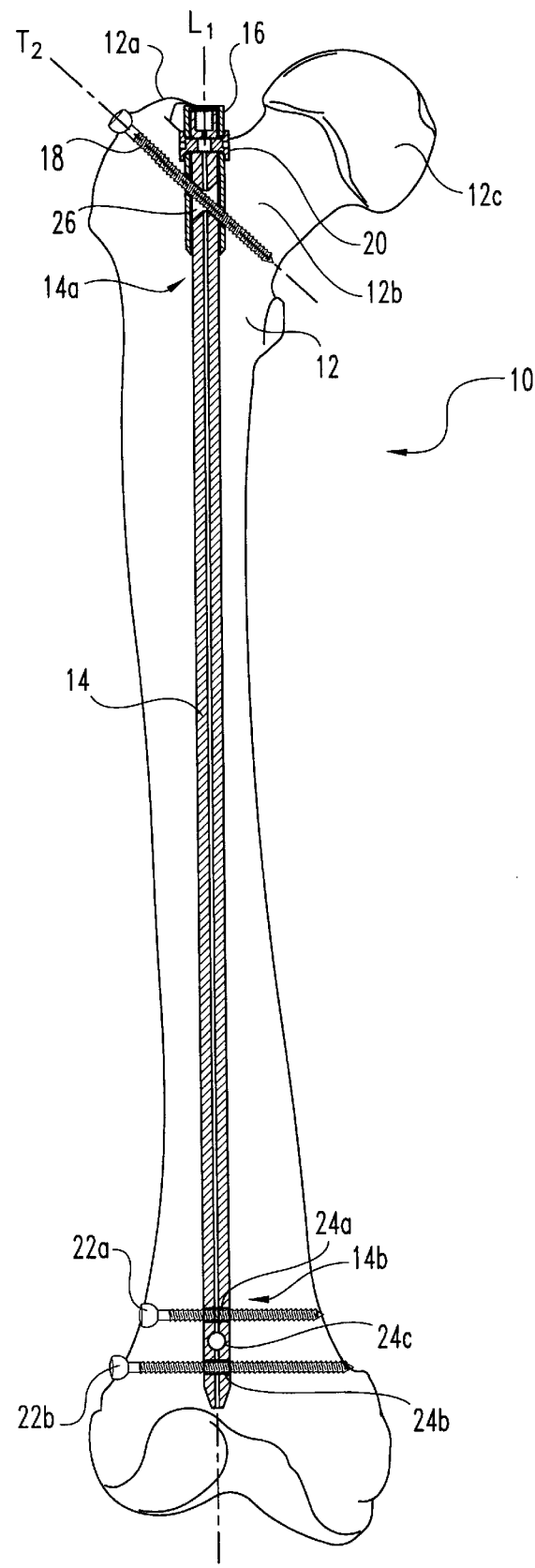
FIG. 1 is a side view, partly in section, of a rod system of the present invention with a transverse member shown in an antegrade position.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein being contemplated as would normally occur to one skilled in the art to which the invention relates.

Figure 2:
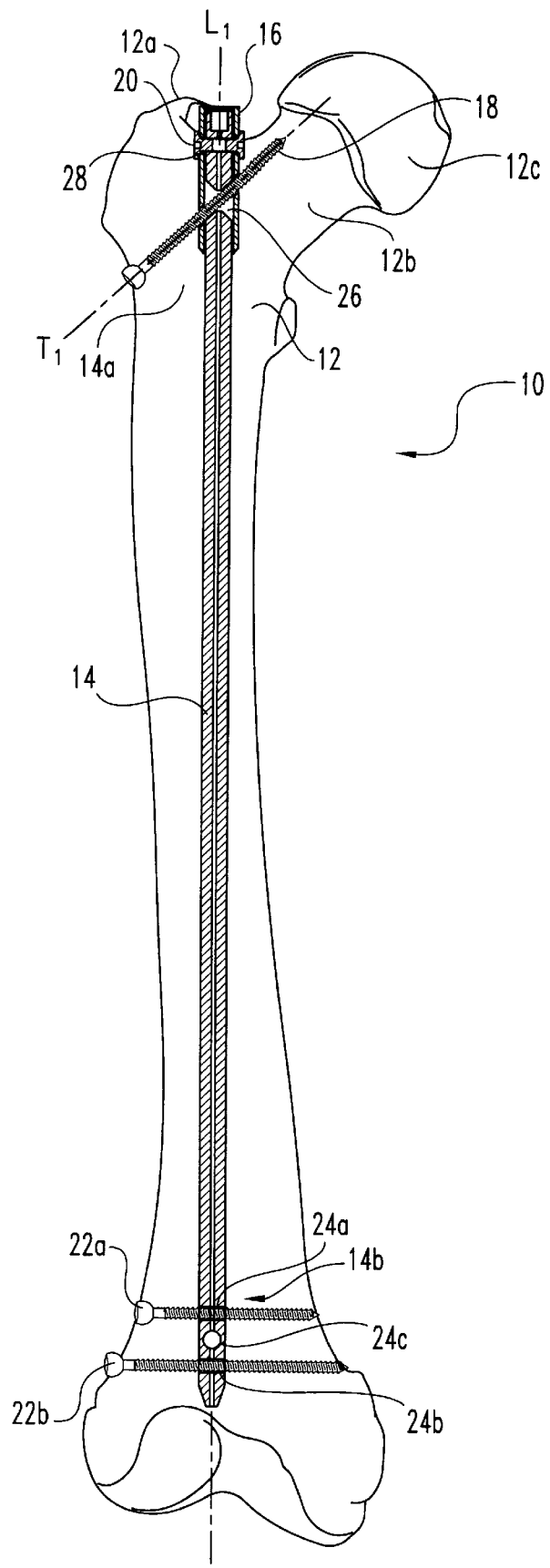
FIG. 2 is a side view, partly in section, of the system of FIG. 1 with the transverse member in a retrograde position.

FIGS. 1–2 depict intramedullary system 10 according to one embodiment of the present invention. System 10 is shown implanted in femur 12 and includes an elongated intramedullary rod or nail 14, sleeve 16 and bone engaging member 18. System 10 also includes fasteners 20 and locking bone screws 22a, 22b. FIG. 1 illustrates system 10 as used in a first locking configuration with bone engaging member 18 placed in an antegrade direction within femur 12. FIG. 2 illustrates a second locking configuration of system 10; where bone engaging member 18 is placed in a retrograde position within femur 12. The tip of the greater trochanter 12a, the neck 12b, and the head 12c of femur 12 are designated in FIGS. 1 and 2. Although system 10 is shown implanted in a human femur 12, system 10 could also be used in conjunction with other bones as would occur to one skilled in the art, including, but not limited to, the tibia, humerus, radius, ulna and fibula.

Nail 14 includes a proximal end portion 14a and a distal end portion 14b. Nail 14 also defines a longitudinal centerline axis $L_1$ running along the length of nail 14 between proximal end portion 14a and distal end portion 14b. For application to an adult human femur, proximal end portion 14a preferably has a diameter of about 11–13 millimeters. The diameter of the remainder of nail 14 may vary depending upon the requirements of the fixation procedure and the surgeon's preference. While nail 14 has a generally circular cross section, other suitable shapes are also contemplated as would occur to one skilled in the art.

Figure 3:
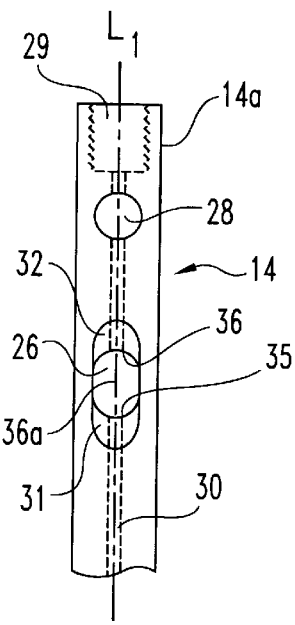
FIG. 3 is a partial side view of the proximal end portion of the rod of FIGS. 1 and 2.
Figure 4:
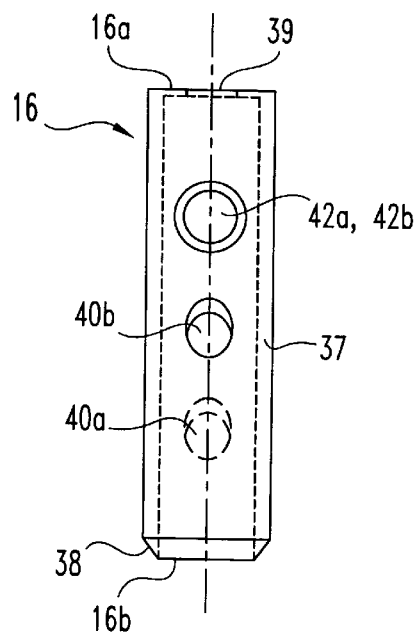
FIG. 4 is a partial side view of the sleeve of FIGS. 1 and 2.
Figure 5:
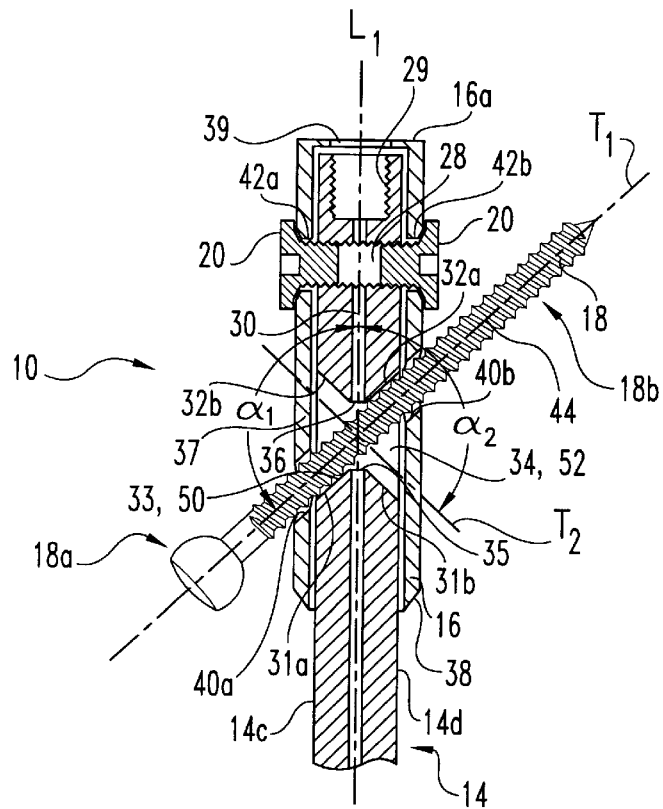
FIG. 5 is a partial, sectional side view of the proximal end portion of the rod shown in FIG. 3 and the sleeve of FIG. 4 assembled together with the locking member of FIGS. 1 and 2.

Referring additionally to FIGS. 3–5, portion 14b of nail 14 defines generally parallel transverse bores 24a, 24b, each sized to respectively receive locking bone screws 22a, 22b therein. Distal end portion 14b also defines transverse bore 24c, aligned generally perpendicular to transverse bores 24a, 24b and sized to receive locking bone screw 22c (not shown). Proximal end portion 14a defines an opening 26 and a threaded transverse bore 28, both extending through nail 14 generally transverse to axis $L_1$ from a first side 14c to a second side 14d. Side 14c generally opposes side 14d. Proximal end portion 14a also defines threaded longitudinal bore 29 generally extending along axis $L_1$ for receiving nail insertion and extraction instrumentation (not shown) used to guide nail 14 into and out of femur 12. Nail 14 also defines a longitudinal passage 30 intersecting bore 29 and extending generally along axis $L_1$ to allow for the optional use of a guide wire (not shown) to aid in the insertion of nail 14 into femur 12.

Referring more specifically to FIGS. 3 and 5, opening 26 is bound by lower surface 31 opposite upper surface 32. Lower surface 31 includes a first angled surface 31a oriented generally parallel to transverse axis $T_1$. Upper surface 32 includes a second angled surface 32a offset from first angled surface 31a along axis $T_1$. Angled surfaces 31a, 32a are generally parallel to transverse axis $T_1$. Transverse axis $T_1$ is aligned at an oblique angle $\alpha_1$ relative to longitudinal axis $L_1$ of nail 14. Angle $\alpha_1$ is preferably in a range of about 120–150 degrees, with the more preferred angle being about 135 degrees. First angled surface 31a and second angled surface 32a cooperate to define pathway 33 generally oriented at angle $\alpha_1$ relative to axis $L_1$. First pathway 33 is sized to receive bone engaging member 18 therethrough.

Lower surface 31 also includes a third angled surface 31b aligned generally parallel to transverse axis $T_2$. Upper surface 32 also includes a fourth angled surface 32b generally offset from third angled surface 31b along axis $T_2$ that is also generally parallel to transverse axis $T_2$. Comparing to FIG. 2, transverse axis $T_2$ is also aligned at an oblique angle $\alpha_2$ relative to longitudinal axis $L_1$ of nail 14. Angle $\alpha_2$ is preferably in a range of about 120–150 degrees, with the more preferred angle being about 135 degrees. Third angled surface 31b and fourth angled surface 32b cooperate to define pathway 34 generally oriented at angle $\alpha_2$ relative to axis $L_1$. Second pathway 34 is sized to receive bone engaging member 18 therethrough.

First angled surface 31a and third angled surface 31b cooperate to define a first projection 35 extending in a longitudinal direction which narrows a dimension of opening 26 within nail 14 along axis $L_1$. Similarly, second angled surface 32a and fourth angled surface 32b cooperate to define a second projection 36 extending in a longitudinal direction generally opposite first projection 35 to further narrow a dimension of opening 26 within nail 14 along axis $L_1$. In a preferred embodiment, each projection 35, 36 defines an apex, resulting in a convergent-divergent throat 36a about midway between sides 14c and 14d of nail 14. However, first projection 35 and second projection 36 could alternatively define any other geometric configuration as would occur to those skilled in the art. For example, first projection 35 and second projection 36 could be rounded. Likewise, in other alternative embodiments, one or more of projections 35, 36 may be absent. While angled surfaces 31a, 31b, 32a, 32b are generally concave to compliment member 18, other shapes are also contemplated as would occur to those skilled in the art. For example, angled surfaces 31a, 31b, 32a, 32b could be flat or have other configurations corresponding to the outer surface of bone engaging member 18.

Referring to FIG. 4, sleeve 16 of system 10 is illustrated therein. Sleeve 16 has a generally cylindrical shape and defines a proximal end 16a, a distal end 16b and a side wall 37. Sleeve 16 is sized to fit over the proximal end of nail 14 as shown in FIG. 3. Distal end 16b is therefore open to allow for passage of proximal end portion 14a therethrough. Sleeve 16 also defines an inwardly tapered edge 38, terminating at distal end 16b, to permit easy sliding of sleeve 16 through bone. Proximal end 16a defines an opening 39 to permit access to threaded bore 29, and thus allow for passage of nail insertion and extraction instrumentation (not shown). Side wall 37 defines offset apertures 40a, 40b positioned on opposite sides of sleeve 16. Apertures 40a, 40b are generally circular and are aligned and sized to receive bone engaging member 18 therethrough. Side wall 37 further defines opposing transverse apertures 42a, 42b positioned on opposite sides of sleeve 16. Apertures 42a, 42b are generally circular and are aligned and sized to receive fastener 20 therethrough.

Referring to FIG. 5, therein is illustrated bone engaging member 18. Bone engaging member 18 includes a proximal end portion 18a and a distal end portion 18b. Bone engaging member 18 has a generally circular cross section and preferably has a diameter of about 5.5–6.5 millimeters for applications treating fractured adult human femurs. Distal end portion 18b includes a means for fixedly engaging and gripping bone 44. Bone engaging member 18 may be a bone screw having a threaded distal end portion 18b as shown in FIG. 5, or a bone blade having distal end portion 18b formed from a plate with a helical twist (not shown). Alternately, distal end portion 18b may be otherwise configured for engaging bone as would occur to those skilled in the art.

As illustrated in FIG. 5, when sleeve 16 is fitted over proximal end portion 14a of nail 14, apertures 40a, 40b of sleeve 16 are positioned to align with opening 26 of nail 14, and register with pathway 33 along transverse axis $T_1$. Collectively, apertures 40a, 40b and opening 26 define passageway 50 coincident with pathway 33. Passageway 50 is bound on one side by first angled surface 31a and on another side by second angled surface 32a. As bone engaging member 18 is slidably received within passageway 50 and guided along transverse axis $T_1$, bone engaging member 18 forms an abutting relationship with either or both of first and second angled surface 31a, 32a. This relationship may be load bearing in nature. Bone engaging member 18 is sized relative to passageway 50 so that its rotational position about axis $L_1$ and its translational position along axis $L_1$ are generally fixed when positioned therethrough.

As illustrated in FIG. 5, when sleeve 16 is fitted over proximal end portion 14a of nail 14, apertures 42a, 42b of sleeve 16 are aligned with bore 28 of nail 14. A fastener 20 is passed through aperture 42a and threaded into bore 28 to thereby releasably secure sleeve 16 to nail 14. Another fastener 20 is passed through aperture 42b and threaded into bore 28 to further secure sleeve 16 to nail 14. While two fasteners 20 are shown to releasably secure sleeve 16 to nail 14, it is also contemplated that a single fastener may be used to sufficiently secure sleeve 16 to nail 14. To avoid interfering with the optional use of a guide wire (not shown) to aid in the insertion of nail 14 into femur 12, fastener 20 has a length which penetrates bore 28 far enough to secure sleeve 16 to nail 14, but without obstructing longitudinal passage 30. In still other embodiments, one or more of fasteners 20, bore 28, and apertures 42a, 42b may not be utilized at all.

Notably, by rotating sleeve 16 180 degrees relative to nail 14, system 10 may be reconfigured from an antegrade orientation of bone engaging member 18 to a retrograde orientation, or vice-versa. Similarly, regardless of which locking configuration is used, the same components of system 10 can be used to treat either a left or right femur by simply rotating sleeve 16 180 degrees relative to nail 14. As a result, apertures 40a, 40b of sleeve 16 are repositioned to align with pathway 34 through opening 26 of nail 14 along transverse axis $T_2$. Collectively, apertures 40a, 40b and opening 26 define passageway 52 which is coincident with pathway 34. Passageway 52 is bound on one side by third angled surface 31b and on another side by fourth angled surface 32b (see FIGS. 2 and 5). As bone engaging member 18 is slidably received within passageway 52 and guided along transverse axis $T_2$, bone engaging member 18 forms an abutting relationship with either or both of the third and fourth angled surfaces 31b, 32b. Preferably, this relationship is suitable for load bearing, and generally fixes member 18 with respect to rotation about axis $L_1$ or translation along axis $L_1$.

In other embodiments of system 10, the angular alignment of bone engaging member 18 relative to axis $L_1$ may be varied by changing the configuration of sleeve 16. More specifically, apertures 40a, 40b can be aligned at an angle other than $\alpha_1$. In these embodiments, first passageway 50 does not fall along transverse axis $T_1$ of nail 14. Thus, as bone engaging member 18 is slidably received within first passageway 50, bone engaging member 18 will contact either first projection 35 or second projection 36, but will not form an abutting relationship with first angled surface 31a or second angled surface 32a. However, the alternative arrangement is still suitable to fix bone engaging member 18 axially and rotationally relative to nail 14.

Referring again to FIGS. 1 and 2, a femur implantation procedure corresponding to system 10 is next described. The implant procedure generally includes forming a longitudinal hole into, and generally parallel with, the medullary canal from a position slightly medial to the tip of the greater trochanter 12a. The longitudinal hole is sized to receive nail 14 therethrough. Preferably, the longitudinal hole is formed by drilling. Sleeve 16 is fitted over proximal end portion 14a of nail 14 and sleeve 16 is secured to nail 14 by threading fasteners 20 into bore 28. As discussed above, system 10 can be used in either a first or second locking configuration depending on the rotational orientation of sleeve 16 relative to nail 14.

FIG. 1 illustrates system 10 in a first locking configuration corresponding to an antegrade configuration for the depicted femur 12. In this first locking configuration, sleeve 16 is secured to nail 14 with apertures 40a, 40b positioned relative to opening 26 of nail 14 to define passageway 52 along transverse axis $T_2$. Nail 14, with sleeve 16 secured thereto, is inserted through the longitudinal hole and into the medullary canal. A transverse hole is formed through femur 12 across the medullary canal corresponding to transverse axis $T_2$. The transverse hole intersects the medullary canal and is sized to receive bone engaging member 18 therein. Preferably this transverse hole also is formed by drilling. Bone engaging member 18 is inserted into the transverse hole and through passageway 52 formed by nail 14 and sleeve 16. As a result, member 18 is preferably secured against translation along axis $L_1$ or rotation about axis $L_1$. When received in passageway 52, member 18 generally extends between a femur entry point slightly lateral to the greater trochanter 12a to a terminal point below the base of neck 12b. Generally parallel bores are formed through femur 12 transverse to the medullary canal and generally perpendicular to axis $L_1$ to align with transverse bores 24a, 24b of nail 14. Preferably these bores are also formed by drilling. Nail 14 is further locked into position by inserting locking bone screws 22a, 22b through femur 12 and into transverse bores 24a, 24b of nail 14.

FIGS. 2 and 5 illustrates system 10 in a second locking configuration corresponding to a retrograde arrangement relative to the depicted femur 12. In this second locking configuration, sleeve 16 is secured to nail 14 with apertures 40a, 40b positioned relative to opening 26 of nail 14 to define passageway 50 along transverse axis $T_1$. The medullary canal is accessed in generally the same manner as described in connection with FIG. 1. Nail 14, with sleeve 16 secured thereto, is inserted through the longitudinal hole medial to the greater trochanter 12a and into the medullary canal. A transverse hole is drilled into femur 12 across the medullary canal corresponding to transverse axis $T_1$ and sized to receive bone engaging member 18 therein. Bone engaging member 18 is inserted into the transverse hole through passageway 50. So arranged, member 18 generally extends through neck 12b into head 12c. Generally parallel bores are formed through femur 12 transverse to the medullary canal and generally perpendicular to axis $L_1$. These bores are generally aligned with transverse bores 24a, 24b of nail 14. Nail 14 is further locked into position by inserting locking bone screws 22a, 22b through femur 12 and into transverse bores 24a, 24b of nail 14.

Next, a preferred method of manufacturing nail 14 is described. This preferred method includes drilling a first bore through proximal portion 14a in a direction corresponding to transverse axis $T_1$ (aligned at angle $\alpha_1$). A second bore is then drilled through proximal portion 14a corresponding to transverse axis $T_2$ (aligned at angle $\alpha_2$) and intersecting the first bore at a point generally corresponding to the centerline of nail 14. The first and second bores are each sized to receive bone engaging member 18 therethrough. The first bore thereby defines first angled surface 31a and second angled surface 32a, and the second bore thereby defines third angled surface 31b and fourth angled surface 32b. The remaining material between lower surface 31 and upper surface 32 may then be removed to form opening 26 through nail 14, having projections 35, 36 as depicted.

Figure 6:
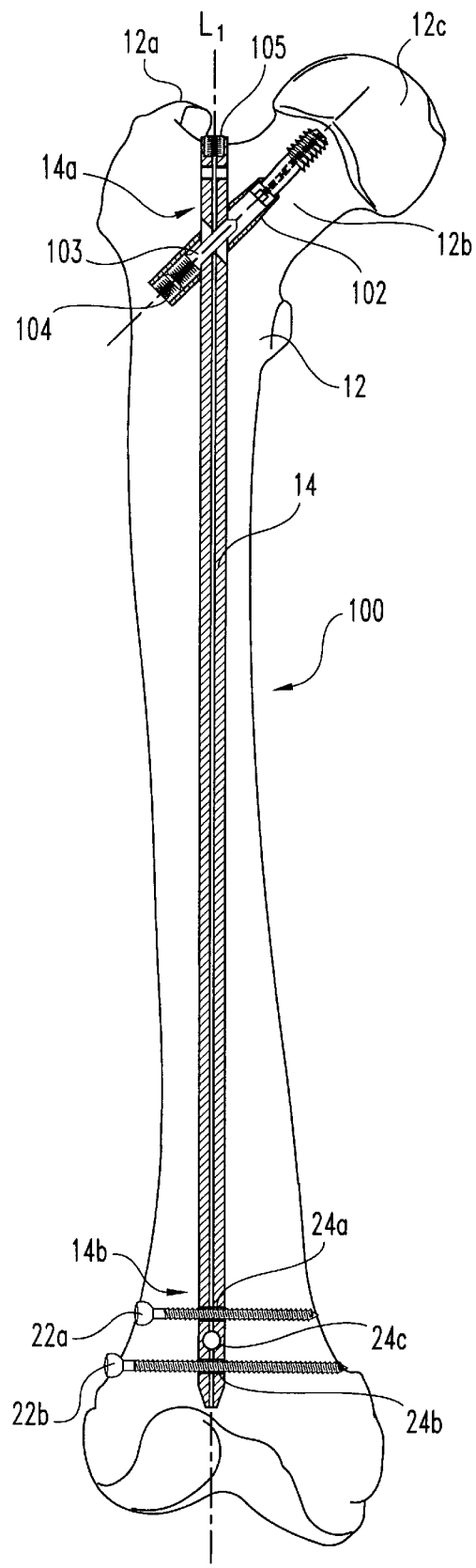
FIG. 6 is a side view, partly in section, of another rod system of the present invention implanted in the neck and head of a femur.

FIG. 6 depicts intramedullary system 100 according to another embodiment of the present invention; where like reference numerals represent like features previously described in connection with system 10. System 100 is shown implanted in femur 12 and includes intramedullary rod or nail 14, transverse member 102, pin 103, locking screw 104 and set screw 105. System 100 also includes locking bone screws 22a, 22b. Although system 100 is shown implanted in human femur 12, system 100 could also be used in conjunction with other bones as would occur to one skilled in the art, including the tibia, humerus, radius, ulna and fibula to name a few. While system 100 could be used to treat the same indications as system 10 in the second locking configuration, as illustrated in FIG. 2 and discussed above, it is preferably used for fractures of the proximal portion of femur 12, and more preferably fractures between the neck 12b and head 12c. The same components of system 100 can be used to treat either a left or right femur by rotating transverse member 102 180 degrees relative to nail 14.

Figure 7:
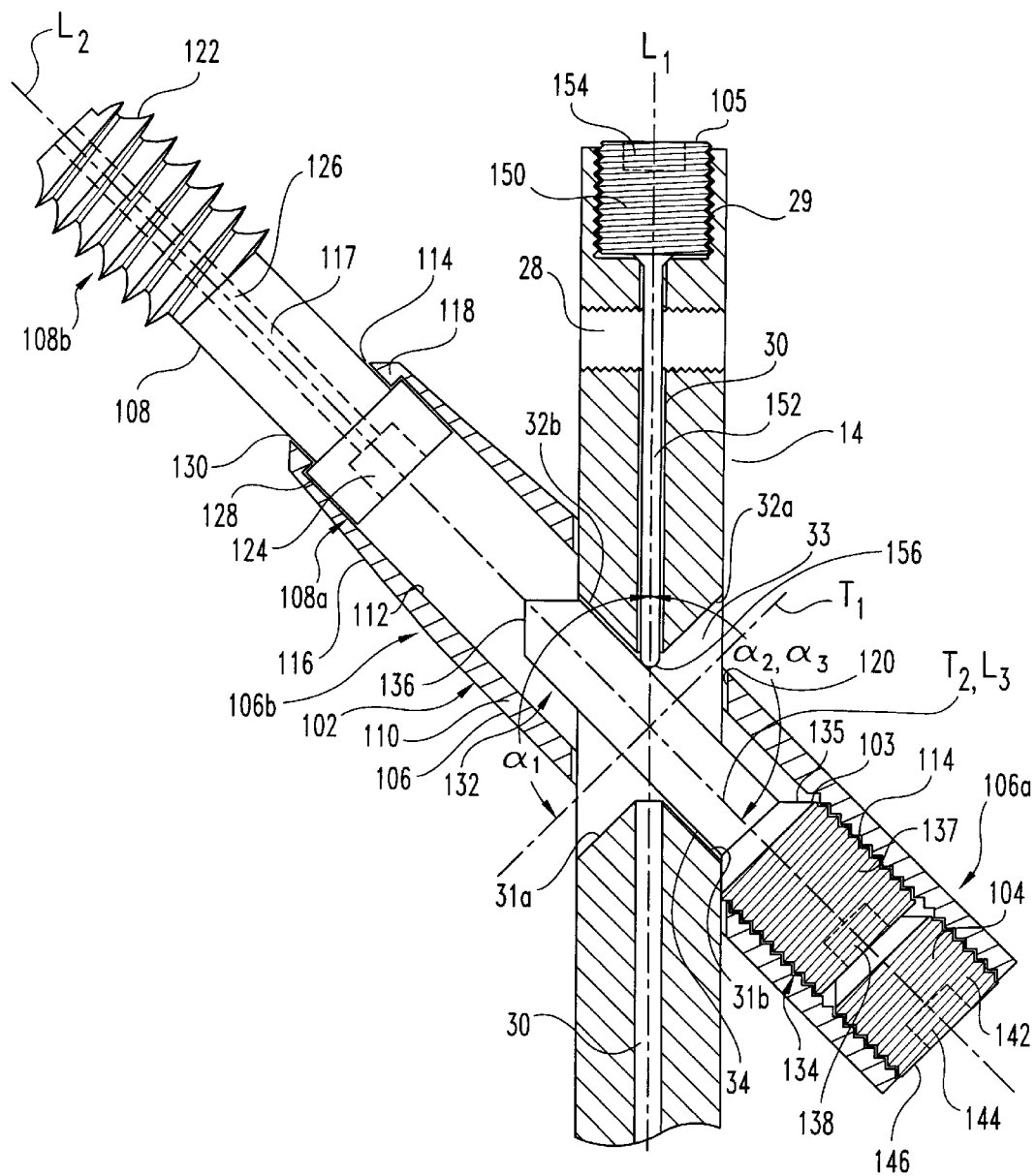
FIG. 7 is a partial, sectional side view of the proximal end portion of the system of FIG. 6.

FIGS. 7–12 provide additional details concerning the structure and assembly of system 100. Referring to FIG. 7, various structural details of transverse member 102 and pin 103 are shown therein. Transverse member 102 defines a longitudinal centerline axis $L_2$ and includes a barrel connection portion 106 and a bone engaging portion 108. Connection portion 106 is generally cylindrical and has a side wall 110. Side wall 110 defines a passage 112 extending generally along axis $L_2$. Connection portion 106 also includes a proximal portion 106a and a distal portion 106b. Proximal portion 106a includes an internal threaded portion 114 extending along a portion of passage 112. Distal portion 106b defines an external inward taper 116 to promote ease of movement through bone when transverse member 102 is advanced into femur 12. Distal portion 106b also defines an inner retaining lip 118 for provisionally maintaining bone engaging portion 108 in sliding engagement with connection portion 106, the operation of which will become apparent hereinafter.

A thru-hole 120 is formed through connection portion 106. Thru-hole 120 is generally cylindrical and has a diameter slightly greater than the outer diameter of proximal portion 14a of nail 14. Alternately, thru-hole 120 could be elliptical or any other shape corresponding to proximal portion 14a of nail 14. Additionally, thru-hole 120 and portion 14a of nail 14 could be asymmetrical and of similar profile to prevent rotational movement of transverse member 102 relative to nail 14 when proximal portion 14a is received within thru-hole 120. Similarly, if thru-hole 120 and portion 14a of nail 14 where both tapered in the same direction and at about the same angle, the resulting tight engagement between transverse member 102 and nail 14 would aid in preventing rotational movement.

Thru-hole 120 is formed through connection portion 102 to provide a selected angular relationship with axis $L_1$ when nail 14 passes therethrough. This relationship corresponds to angle $\alpha_3$ between axes $L_1$ and $L_2$, and is preferably in a range of about 130–145 degrees. More preferably, for system 100, angle $\alpha_3$ is about 135 degrees and is equal to angle $\alpha_2$ as depicted in FIG. 6. As will become apparent from later discussion, angle $\alpha_3$ corresponds to the angle of fixation between transverse member 102 and nail 14.

Bone engaging portion 108 includes a proximal portion 108a and a distal portion 108b. A bone engaging and gripping thread 122 is formed on distal portion 108b. Additionally or alternatively, a different bone gripping means may be utilized, such as a bone blade having distal portion 108b formed from a plate with a helical twist, or such other means as would occur to those skilled in the art.

Proximal portion 108a includes a hex recess 124 for receiving a driving tool (not shown), such as an Allen wrench, preferably suited to drive bone engaging portion 108 into neck 12b and head 12c of femur 12. Bone engaging portion 108 defines a longitudinal passage 126 extending therethrough and generally along axis $L_2$ to allow for the optional use of a guide wire (not shown) to aid in the insertion of bone engaging portion 108 into bone. Proximal portion 108a is sized to be received within passage 112 of connection portion 106 to allow slidable movement of bone engaging portion 108 generally along axis $L_2$ over a predetermined range. A keeper 128 is provided on, in association with, or integral to proximal portion 108a to provisionally maintain bone engaging portion 108 and connection portion 106 in a telescopic sliding relationship. Keeper 128 is comprised of a cylindrical sleeve that is preferably laser welded onto shaft 130 of bone engaging portion 108 after it has been positioned within connection portion 106. The outer diameter of keeper 128 is slightly smaller but in close tolerance with the inner diameter of passage 112.

Figure 8B:
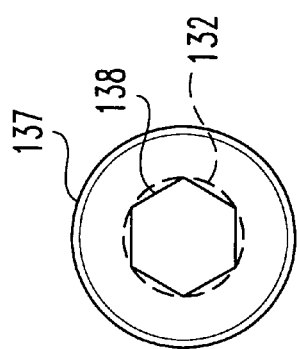
FIG. 8B is an end view of the fixed angle pin of FIG. 7.
Figure 8A:
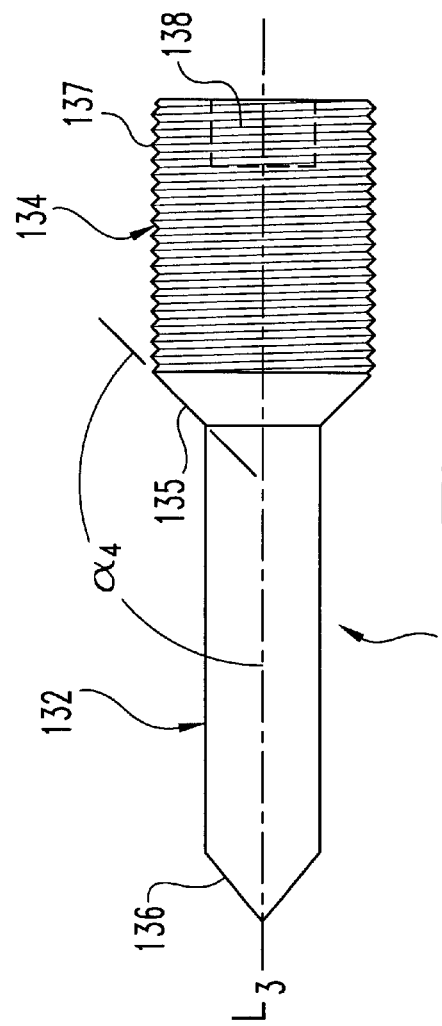
FIG. 8A is a side view of the fixed angle pin of FIG. 7.

Pin 103 is shown positioned within passage 112 of connection portion 106. FIGS. 8A and 8B additionally illustrate various structural details of pin 103. Pin 103 has a longitudinal centerline axis $L_3$ and includes a leading portion 132 integrally connected to a trailing portion 134. Leading portion 132 has a generally circular, elongated body and is sized to be received within opening 26 of nail 14. Leading portion 132 also includes an angled, annular engaging surface 135 configured to co-act with a surface of nail 14. Engaging surface 135 is aligned at an angle $\alpha_4$ relative to axis $L_3$. Angle $\alpha_4$ is in a range of about 130–145 degrees. Most preferably, angle $\alpha_4$ should be approximately equal to angle $\alpha_2$. Leading portion 132 additionally includes a tapered tip 136. Trailing portion 134 is provided with an externally threaded portion 137 configured to threadedly engage threaded portion 114 of connection portion 106. A hex recess 138 is defined by trailing portion 134 for receiving a driving tool (not shown), such as an Allen wrench, to advance pin 103 into portion 106 or remove pin 103 from portion 106 by turning in a corresponding rotational direction. In other embodiments, pin 103 additionally or alternatively has a different means for positioning relative to connection portion 106, such as a ratcheting mechanism, a cabling arrangement, or any other method capable of advancing pin 103 along axis $L_2$ as would occur to those skilled in the art.

In order to prevent pin 103 from migrating once positioned in a desired position within passage 112, system 100 includes locking screw 104. Locking screw 104 is provided with external threads 142 configured to threadedly engage threaded portion 114 of connection portion 106. A hex recess 144 is defined by trailing end 146 for receiving a driving tool (not shown), such as an Allen wrench, to rotationally advance locking screw 104 along connection portion 106. Locking screw 104 is axially advanced along axis $L_2$ until it tightly engages trailing portion 134 of pin 103. In other embodiments, system 100 additionally or alternatively includes another locking means as would normally occur to one skilled in the art to prevent pin 103 from migrating relative to connection portion 106.

To further aid in preventing pin 103 from rotating, loosening or migrating once positioned in a desired axial position within passage 112, system 100 includes set screw 105. Set screw 105 includes a threaded portion 150 and an elongated stem portion 152. Threaded portion 150 is configured to threadedly engage bore 29 of nail 14. Threaded portion 150 also includes a hex recess 154 for receiving a driving tool (not shown), such as an Allen wrench, to rotationally advance set screw 105 along bore 29. Elongated stem portion 152 is sized to be slidably received within longitudinal passage 30 of nail 14. Stem 152 also defines a tapered or contoured end 156 conforming with an outer surface of leading portion 132 of pin 103 to provide improved mechanical interlocking between set screw 105 and pin 103.

Referring generally to FIGS. 6, 7, 8A, and 8B, another embodiment of a femur implantation procedure in accordance with the present invention is described with respect to system 100. This femur implantation procedure generally includes forming a transverse passage into femur 12 that crosses the medullary canal and is sized to receive transverse member 102 therein. Preferably, this transverse passage is formed by drilling and begins at the lateral side of femur 12, extends into neck 12b and terminates in head 12c to orient transverse member 102 as depicted in FIG. 6. Also shown in FIG. 6, it is preferred that the transverse passage form an oblique angle approximately the same as angle $\alpha_3$ with respect to axis $L_1$ or the medullary canal.

Next, transverse member 102 is introduced through the transverse passage with thru-hole 120 positioned to at least overlap the medullary canal of femur 12, and preferably to be generally centered with respect to the medullary canal of femur 12. At least a portion of bone engaging portion 108 is threaded into femur 12 at this stage. Preferably, bone engaging portion 108 is threaded into a portion of head 12c of femur 12 by engaging hex recess 124 with a suitable tool and turning portion 108 in a corresponding rotational direction generally about axis $L_2$.

Notably, bone engaging portion 108 is telescopically received within passage 112 of connection portion 106 to allow axial movement of bone engaging portion 108 over a predetermined range along axis $L_2$. Keeper 128 cooperates with inner retaining lip 118 to prevent disengagement of bone engaging portion 108 from connection portion 106. The cooperation between inner retaining lip 118 and keeper 128 also acts to stabilize bone engaging portion 108, thus aiding in the sliding motion of bone engaging portion 108 to provide the preferred telescopic functioning of transverse member 102. Since connection portion 106 provisionally maintains bone engaging portion 108 in a captive, telescopic relationship, the alignment of bone engaging portion 108 along axis $L_2$ is always maintained. Thus, when the procedure includes turning thread 122 through neck 12b of femur 12 and into head 12c, head 12c will become fixed in an angular relationship relative to transverse member 102. By maintaining the angular alignment between neck 12b and head 12c, and allowing them to slide telescopically relative to one another, system 100 can accommodate for changes during patient movement and expedite the bone healing process.

After transverse member 102 is inserted, an opening is formed, preferably by drilling, into and generally along the medullary canal from a position slightly medial relative to the tip of the greater trochanter 12a and sized to receive nail 14 therethrough. Nail 14 is inserted through the longitudinal hole and into the medullary canal. Nail 14 passes through thru-hole 120 of connection portion 106. Thru-hole 120 of transverse member 102 receives nail 14 in a close sliding fit, thereby permitting limited axial and rotational movement of transverse member 102 along axis $L_1$ of nail 14. Transverse member 102 is longitudinally positioned on nail 14 so that passage 112 of connection portion 106 registers with opening 26 of nail 14. If desired, bone engaging portion is further advanced into the bone at this stage.

Next, pin 103 is axially advanced through passage 112 by engaging hex recess 144 with an appropriate tool and rotating in a corresponding direction. As threaded portion 137 of pin 103 engages threaded portion 114 of connection portion 106, leading portion 132 is slidably received within opening 26 to engage one or more surfaces 31b, 32b. Even if passage 112 and opening 26 are misaligned, in many instances tapered tip 136 allows pin 103 to self-center, thereby aiding in the insertion of leading portion 132 within opening 26. As pin 103 is slidably received within pathway 34 of opening 26 and guided along transverse axis $T_2$, leading portion 132 forms an abutting relationship with one or both of angled surfaces 31b, 32b. Pin 103 thus becomes oriented at angle $\alpha_2$ relative to axis $L_1$, aiding in the fixation of transverse member 102 relative to nail 14. As pin 103 is further advanced through passage 112, engaging surface 135 is firmly pressed against nail 14 and transverse member 102 is pulled in a proximal direction. Correspondingly, an inner surface of transverse member 102 that borders thru-hole 120 is clamped against an outer surface of nail 14 while generally maintaining angle $\alpha_2$ of transverse member 102 relative to axis $L_1$.

After securely clamping transverse member 102 and nail 14 together, generally parallel passages are formed, preferably by drilling through femur 12 transverse to the medullary canal and aligned with transverse bores 24a, 24b of nail 14. Nail 14 is further locked into position by inserting locking bone screws 22a, 22b through femur 12 and into transverse bores 24a, 24b of nail 14.

Figure 9:
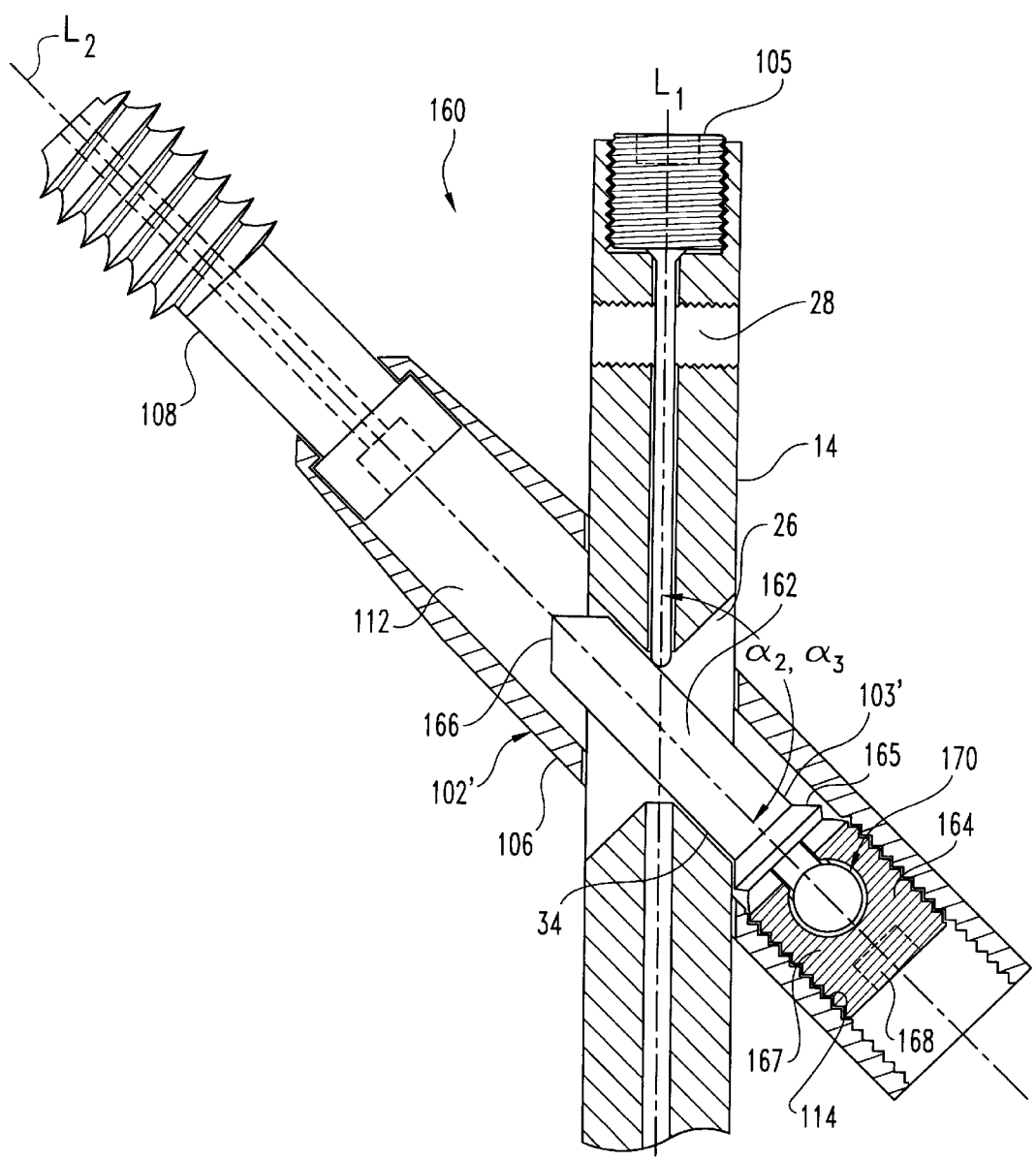
FIG. 9 is a partial, sectional side view of the proximal end of yet another system of the present invention having a variable angle pin positioned at 135 degrees relative to a rod.
Figure 10A:
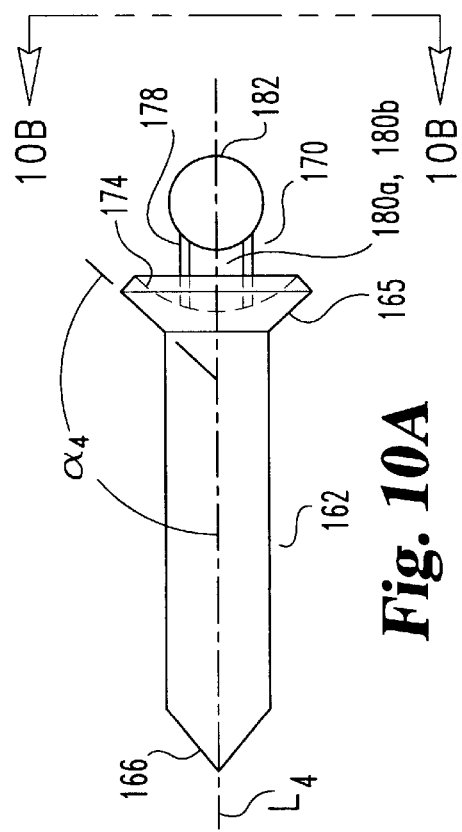
FIG. 10A is a side view of the leading portion of the variable angle pin of FIG. 9.
Figure 10B:
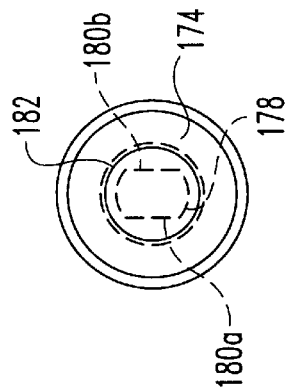
FIG. 10B is an end view of the leading portion of the variable angle pin of FIG. 9 taken along view line 10B—10B of FIG. 10A.
Figure 11A:
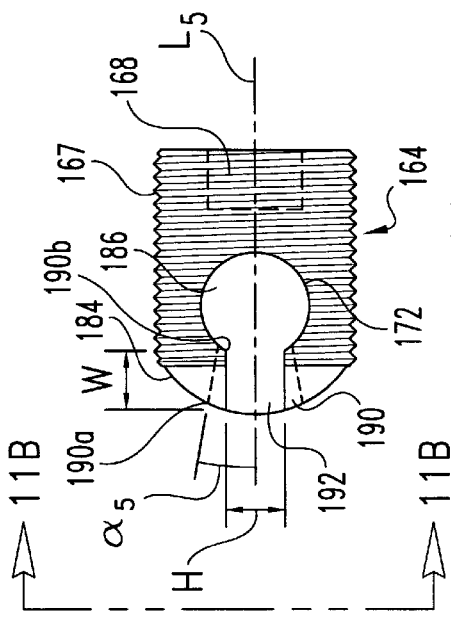
FIG. 11A is a side view of the trailing portion of the variable angle pin of FIG. 9.
Figure 11B:
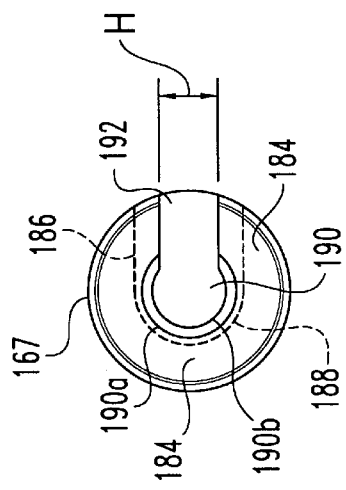
FIG. 11B is an end view of the trailing portion of the variable angle pin of FIG. 9 taken along view line 11B—11B of FIG. 11A.

Referring to FIG. 9, system 160 of another embodiment of the present invention is illustrated; where reference numerals like those of previous embodiments refer to like features. System 160 includes transverse member 102' which is the same as transverse member 102 except that pin 103' is utilized in place of pin 103. FIGS. 10A, 10B, 11A and 11B illustrate selected details of pin 103'. Pin 103' includes a leading portion 162 and a non-integral trailing portion 164. Leading portion 162 preferably has a generally circular, elongated body and is sized to be received within opening 26 of nail 14. Leading portion 162 also includes an angled, annular engaging surface 165 configured to co-act with a surface of nail 14. Engaging surface 165 is aligned at an angle $\alpha_4$ relative to axis $L_4$ of pin 103'. Leading portion 162 additionally includes a tapered tip 166.

Leading portion 162 is articulated to trailing portion 164 to facilitate pivotal movement of portion 162 relative to portion 164. Trailing portion 164 includes externally threaded portion 167 configured to threadedly engage threaded portion 114 of connection portion 106. A hex recess 168 is defined by trailing portion 164 for receiving a driving tool (not shown), such as an Allen wrench, to advance pin 103' axially along connection portion 106. In other embodiments, pin 103' is alternatively or additionally configured with a different means to be axially advanced through connection portion 106, such as a ratcheting mechanism or a cabling arrangement. In still other embodiments, techniques are utilized as would occur to one skilled in the art.

Leading portion 162 has a longitudinal centerline axis $L_4$ and trailing portion 164 has a longitudinal centerline axis $L_5$. Unlike pin 103, leading portion 162 and trailing portion 164 are not integral and are coupled to permit leading portion 162 to pivot relative to trailing portion 164. This pivoting or articulation permits angular variation of portion 162 relative to axis $L_2$. In one preferred embodiment, leading portion 162 includes a ball and socket joint 170 to provide the angular adjustment capability.

The rear portion of leading portion 162 defines a concave surface 174 generally centered about axis $L_4$. Projecting proximally from concave surface 174 along axis $L_4$ is stem 178. Stem 178 has a generally circular cross section, but also preferably defines a pair of parallel, opposing flats 180a, 180b. A ball member 182 is positioned at the end of stem 178 and is generally spherical-shaped. Trailing portion 164 defines a convex surface 184 generally centered about axis $L_5$ and configured to closely conform with concave surface 174 of leading portion 162. Trailing portion 164 also defines a transverse socket 186 extending partially therethrough and aligned generally perpendicular to axis $L_5$.

Transverse socket 186 has a diameter slightly larger than the diameter of ball member 182. Transverse socket 186 terminates at concave bottom surface 188. Concave bottom surface 188 substantially conforms with the outer surface of ball member 182. Trailing portion 164 also defines a longitudinal bore 190 aligned with axis $L_5$. Longitudinal bore 190 extends from convex surface 184 to transverse socket 186. Longitudinal bore 190 is outwardly tapered with wide end 190a intersecting convex surface 184 and narrow end 190b intersecting transverse socket 186, thus defining taper angle $\alpha_5$ relative to axis $L_5$. Preferably, taper angle $\alpha_5$ is between about 5 degrees and 20 degrees. Most preferably, taper angle $\alpha_5$ is about 10 degrees. Trailing portion 164 further defines a transverse slot 192 extending partially therethrough and substantially aligned with transverse socket 186. Slot 192 has a width W extending along longitudinal bore 190 from convex surface 184 to transverse socket 186. Slot 192 has a depth sufficient to intersect narrow end 190b of transverse bore 190. Height H of slot 192 is slightly greater than the distance between flats 180a, 180b of stem 190. Collectively, socket 186 and slot 192 are configured to receive ball member 182 and stem 178 therein, respectively.

In another embodiment of pin 103', a flexible, readily deformable intermediate section is positioned between leading portion 162 and trailing portion 164 that may be additionally or alternatively used to provide means for allowing angular variation between axis $L_4$ and axis $L_5$. In still another embodiment, portion 162 is journaled to portion 164 by a shaft through a bore, permitting rotation of portion 162 relative to portion 164. In other embodiments, another suitable means for providing angular variation between axis $L_4$ and $L_5$ may alternatively or additionally be utilized as would occur to those skilled in the art.

As illustrated in FIG. 9, pin 103' operates generally in the same manner as pin 103 described in connection with system 100. Although pin 103' can be used in instances where angles $\alpha_2$ and $\alpha_3$ are substantially equal (as shown in FIG. 9), the more preferred application arises in configurations where angles $\alpha_2$ and $\alpha_3$ are different. The articulation of leading portion 162 relative to trailing portion 164 facilitates secure clamping to nail 14 despite a mismatch between the angled surfaces 31a, 32a, or 31b, 32b and the angular relationship of member 102' to axis $L_1$ defined by thru-hole 120. For example, referring additionally to FIG. 12, angles $\alpha_2$ and $\alpha_3$ are about 135 and 140 degrees, respectively, relative to axis $L_1$. Preferably, the pivot range of leading portion 162 accommodates a range of different angular orientations of thru-hole 120 corresponding to $\alpha_3$. In one more preferred range, leading portion 162 pivots to accommodate a variation of angle $\alpha_3$ from about 130 to about 145 degrees.

In one preferred implantation procedure, transverse member 102' and nail 14 are implanted in accordance with the same procedure for inserting bone engaging member 108, connection portion 106 and nail 14, with the engagement of pin 103' in place of pin 103. For pin 103', ball member 182 is inserted into socket 186 by aligning flats 180a, 180b of stem 178 with slot 192 and then guiding ball member 182 within transverse socket 186 until ball member 182 is positioned adjacent concave bottom surface 188. A slight rotation or angulation of leading portion 162 relative to trailing portion 164 securely engages the two portions. As a result, leading portion 162 is rotatably coupled to trailing portion 164 by ball and socket joint 170. Thus, leading portion 162 can rotate freely over a predetermined range within passage 112 as limited by taper angle $\alpha_5$. In one preferred embodiment, taper angle $\alpha_5$ permits angular variation between leading portion 162 and trailing portion 164 of about 10 degrees in any direction. The assembly of leading portion 162 to trailing portion 164 may be performed during the implantation procedure just before insertion into passage 112 or in advance of the procedure as desired.

Figure 12:
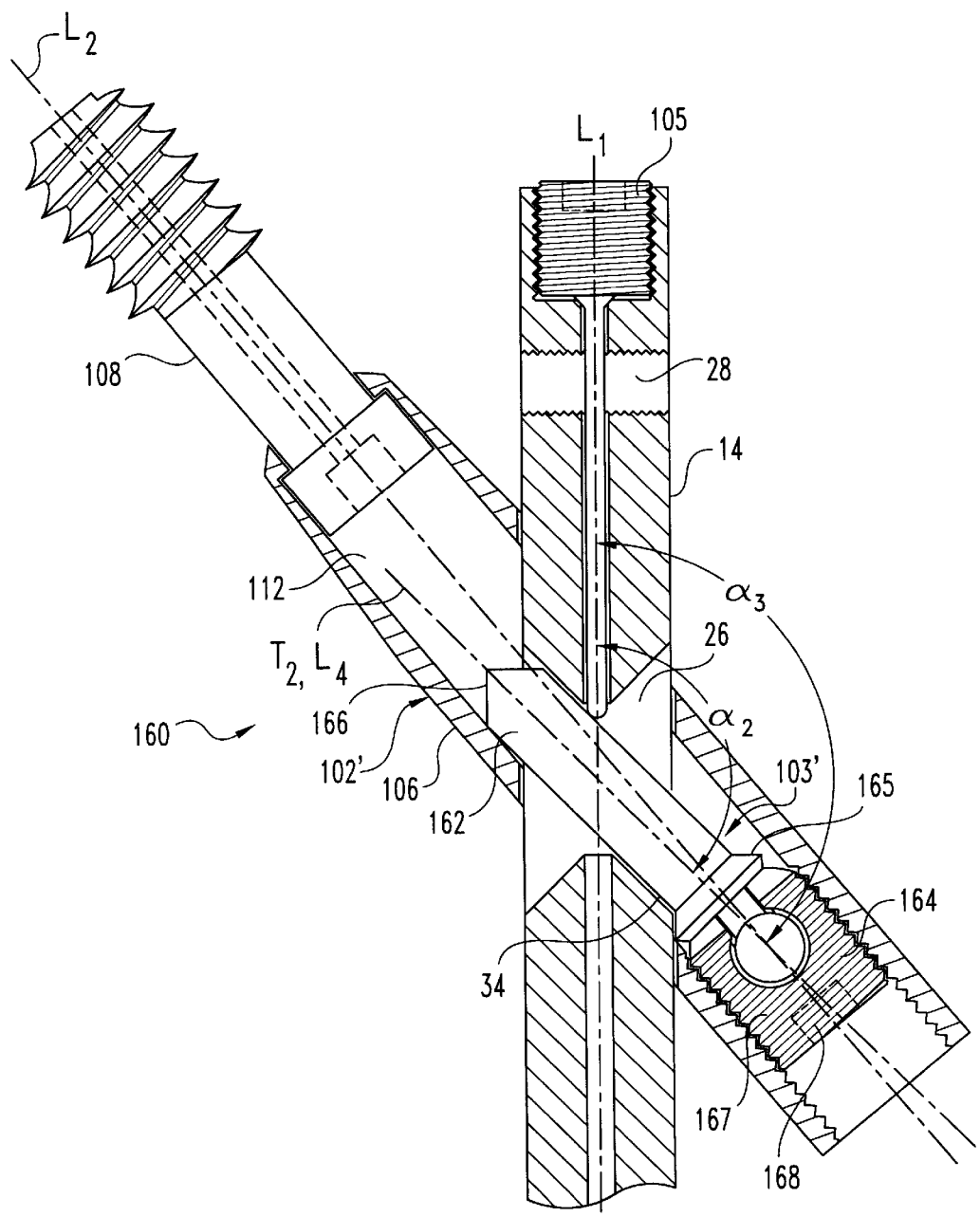
FIG. 12 is a partial, sectional side view of the proximal end of the system of FIG. 9 showing the variable angle pin at 140 degrees relative to the rod.

Once leading portion 162 and trailing portion 164 are assembled, Pin 103' is advanced through passage 112 of connection portion 106 by engaging hex recess 168 and turning in the appropriate rotational direction. Pin 103' is slidably received within pathway 34 of opening 26 and leading portion 162 is guided along transverse axis $T_2$ to form an abutting relationship with one or both of angled surfaces 31b, 32b. If, as mentioned above, thru-hole 120 is disposed in connection portion 106 in correspondence to a different angle $\alpha_3$ relative to axis $L_1$ (such as 140 degrees), leading portion 162 is forced to pivot relative to trailing portion 164 and thereby aligns at angle $\alpha_2$ (such as 135 degrees). As trailing portion 164 is tightened in connection portion 106, a rigid, secure construct forms between transverse member 102' and nail 14 as described in connection with the operation of system 100, except that pin 103' may pivot, contacting an inner surface of connection portion 106 as illustrated in FIG. 12. Notably, like system 10, system 100 and 160 may be reconfigured to accommodate either the left or right femur or an antegrade or retrograde application; however, in other embodiments of the present invention, rod 14 may be modified to define only one generally linear pathway therethrough.

Figure 13:
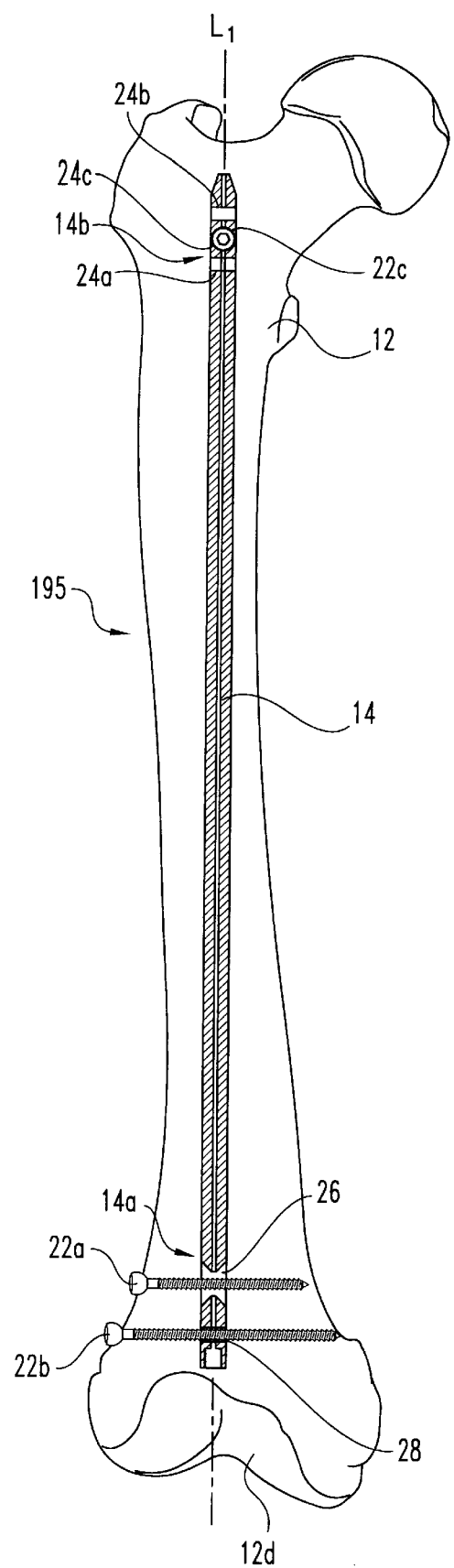
FIG. 13 is a side view, partly in section, of still another rod system of the present invention illustrating implantation of an intramedullary nail inserted in a retrograde direction.

Referring now to FIG. 13, system 195 according to another embodiment of the present invention is illustrated; where reference numerals of previously described embodiments refer to like features. Preferably, system 195 is implanted in femur 12 as shown, and includes intramedullary rod or nail 14, set screw 105, and locking bone screws 22a, 22b, 22c. In other embodiments, system 195 may be used in conjunction with other bones as would occur to one skilled in the art, such as the tibia, humerus, radius, ulna, or fibula to name a few. Additionally, the same components of system 195 can be used to treat either a left or right femur by simply rotating nail 14 180 degrees relative to longitudinal axis $L_1$. Unlike systems 10, 100 and 160; system 195 positions nail 14 with the proximal and distal end portions reversed within femur 12 corresponding to implantation of nail 14 in a retrograde direction. Unlike existing systems, nail 14 need not be modified to operate in a retrograde direction. Indeed, nail 14 may be used in either an antegrade direction, as illustrated in connection with systems 10, 100, and 160, or a retrograde direction as illustrated in FIG. 13.

One preferred implant procedure for system 195 includes forming a longitudinal hole along femur 12, intersecting the medullary canal from a point generally central to distal end portion 12d. The longitudinal hole is sized to receive nail 14 therethrough and is preferably formed by drilling into femur 12. Nail 14 is inserted through the longitudinal hole and into the medullary canal. A pair of generally parallel, transverse passageways are formed, preferably by drilling, through femur 12 transverse to and intersecting with the medullary canal. These passageways are in registry with opening 26 and transverse bore 28, respectively. Nail 14 is locked into position by inserting locking bone screws 22a, 22b into the transverse passageways and correspondingly through opening 26 and transverse bore 28. Another transverse passageway is drilled through femur 12 across the medullary canal and intersecting therewith that is generally aligned with transverse bore 24c formed in distal portion 14b of nail 14. Nail 14 is further locked into position by inserting locking bone screw 22c into this distal transverse passageway and correspondingly through transverse bore 24c. Although system 195 does not require a sleeve to lock bone screws 22a, 22b into position relative to nail 14, as discussed below, such a feature may optionally be utilized.

Figure 14:
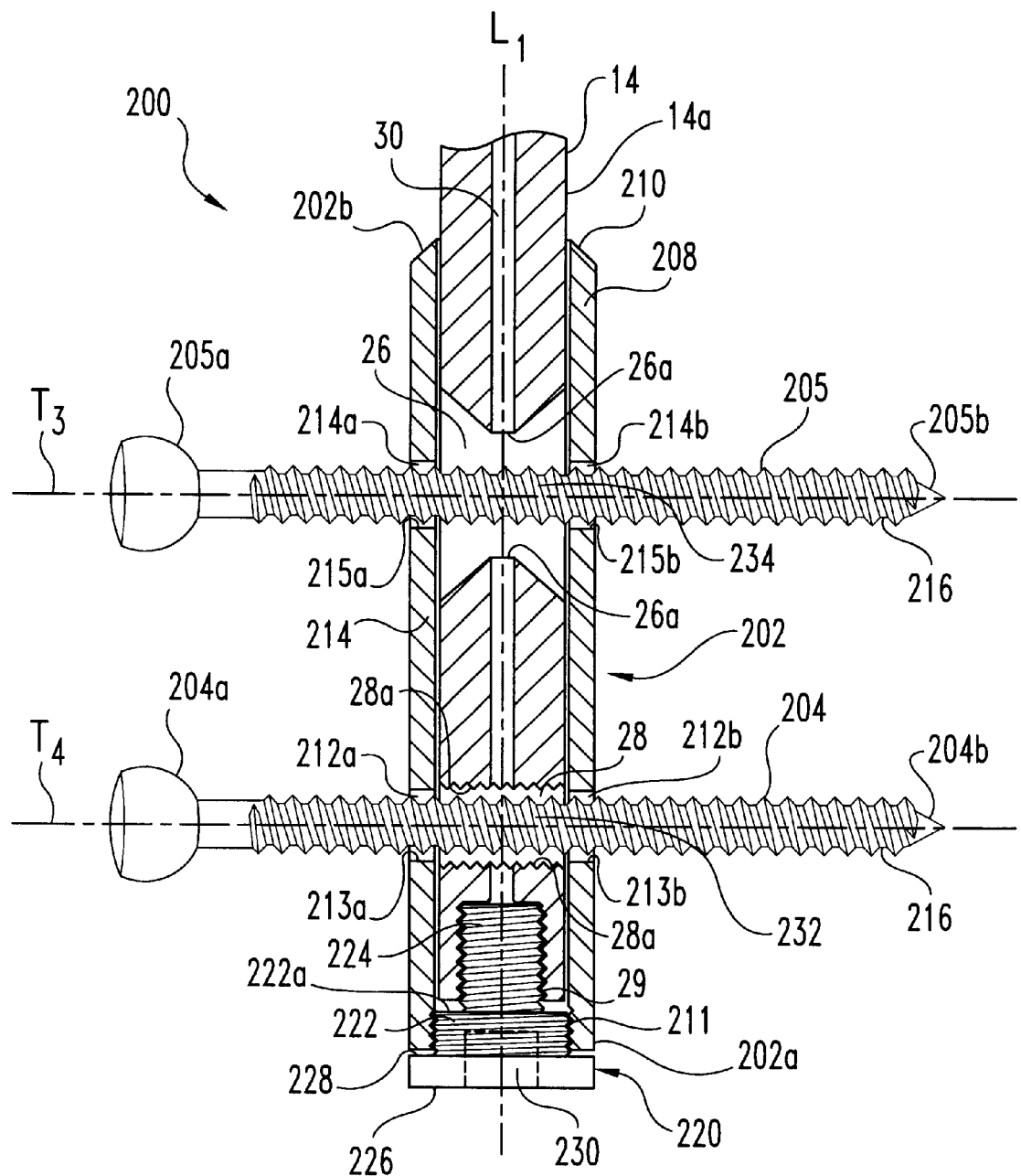
FIG. 14 is a partial, sectional side view of the proximal end portion of a further system of the present invention.

Referring now to FIG. 14, shown is bone treatment system 200 according to yet another embodiment of the present invention; where reference numerals of previously described embodiments refer to like features. System 200 is shown implanted in femur 12 and includes intramedullary nail 14, sleeve 202, bone engaging members 204, 205 and biasing sleeve 202. Preferably, system 200 is utilized to treat fractures of the human femur, but may be used in conjunction with any other bone as would occur to those skilled in the art. Additionally, while system 200 can be used with any nail and sleeve configuration, it is preferably used in conjunction with retrograde implantation of nail 14 as described in connection with FIG. 13 herein.

In FIG. 14, opening 26 extends generally along transverse centerline axis $T_3$ and transverse bore 28 extends generally along transverse centerline axis $T_4$. Opening 26 is bounded by a bearing surface 26a and bore 28 is bounded by a bearing surface 28a. Sleeve 202 has a generally cylindrical shape and defines a proximal end 202a, a distal end 202b, and a side wall 208. Sleeve 202 is sized to fit over proximal end portion 14a of nail 14. Distal end 202b is therefore open to allow for passage of proximal end portion 14a. Sleeve 202 defines an inwardly tapered edge 210, terminating at distal end 202b, to facilitate movement of sleeve 202 through bone. Proximal end 202a is also open to allow for the passage of nail insertion and extraction instrumentation (not shown). The interior surface of side wall 208 immediately adjacent proximal end 202a defines a threaded portion 211. Side wall 208 also defines two sets of opposing apertures 212a, 212b and 214a, 214b. Apertures 212a, 214a oppose apertures 212b, 214b in a direction along axes $T_3$, $T_4$, respectively. Aperture sets 212a, 212b, and 214a, 214b are generally circular and are aligned and sized to respectively receive bone engaging members 204, 205 therethrough. Apertures 212a, 212b define circumferential engaging surfaces 213a, 213b, respectively, and apertures 214a, 214b define circumferential engaging surfaces 215a, 215b, respectively.

Bone engaging member 204 includes a proximal end portion 204a opposite a distal end portion 204b. Bone engaging member 204 has a generally circular cross section and preferably has a diameter of about 5.5–6.5 millimeters for a femur application. Distal end portion 204b includes thread 216 for engaging and gripping bone. Alternatively or additionally, member 204 may include a different bone engaging or gripping means such as a bone blade having distal end portion 204b formed from a plate with a helical twist or an expansion device. Bone engaging member 205 includes a proximal end 205a and a distal end 205b and is preferably configured the same as bone engaging member 204.

System 200 includes biasing end cap 220. End cap 220 is generally circular and includes a first threaded portion 222 configured to threadingly engage threaded portion 211 of sleeve 202. A second threaded portion 224 is configured to threadingly engage longitudinal bore 29 of nail 14. End cap 220 proximally terminates in an enlarged, flat end portion 226 having protruding flange 228. Flat end portion 226 also defines hex recess 230 for receiving a driving tool (not shown).

System 200 is utilized in accordance with one preferred femur implantation procedure by inserting nail 14 as described in connection with FIG. 13, except, proximal end 14a also carries sleeve 202 thereon by loosely threading end cap 220 into sleeve 202 and rod 14. Accordingly, protruding flange 228 of flat end portion 226 bears against proximal end 202a of sleeve 202. With sleeve 202 so oriented, apertures 212a, 212b are generally in alignment with transverse bore 28 along axis $T_4$ to define passageway 232. Correspondingly, apertures 214a, 214b are generally aligned with opening 26 along transverse axis $T_3$ to defined passageway 234.

Once the nail 14 and sleeve 202 are in place within femur 12, two transverse passages are formed through the bone that are in registry with passageways 232, 234. Next, bone engaging members 204, 205 are received through the bone and passageways 232, 234, respectively. Once bone engaging members are in place. Sleeve 202 is biased by further tightening of end cap 220. As end cap 220 is tightened, is moves sleeve 202 and nail 14 in opposite directions along axes $L_1$. Correspondingly, surfaces 213a, 213b move to bear against bone engaging member 204 and engaging surfaces 214a, 214b bear against bone engaging member 205. In turn, bone engaging member 204 is tightly clamped against bearing surface 26a of opening 26 and bone engaging member 205 is tightly clamped against bearing surface 28a of bore 28. The tight engagement between bone engaging members 204, 205 and bearing surfaces 26a, 28a thereby clamps bone engaging members 204, 205 into position relative to nail 14 and prevents lateral migration. Locking nuts, which have in the past been used to prevent such lateral migration, are generally not needed for system 200, so that additional surgical incisions normally required to engage locking nuts onto the bone engaging members need not be made and soft tissue irritation commonly associated with the presence of the locking nuts is also eliminated. Preparations and implantation of one or more bone engaging members may optionally be performed at distal end 14b of nail 14.

In an alternative embodiment, end cap 220 does not include first threaded portion 222. Thus, as threaded portion 224 engages longitudinal bore 29 of nail 14, flange 228 of flat end portion 226 contacts proximal end 202a of sleeve 202 to advance sleeve 202 in a distal direction relative to nail 14. In still another embodiment, end cap 220 does not include second threaded portion 224. Thus, as threaded portion 222 engages threaded portion 211 of sleeve 202, flat end 222a of threaded portion 222 is forced into contact with the proximal end of nail 14, thereby advancing sleeve 202 in a proximal direction relative to nail 14. In yet another embodiment of system 200, the biasing means consists of a spring member operably captured between nail 14 and sleeve 202. The spring member is configured to urge sleeve 202, nail 14, or both to clamp bone engaging members 204, 205.

Figure 15:
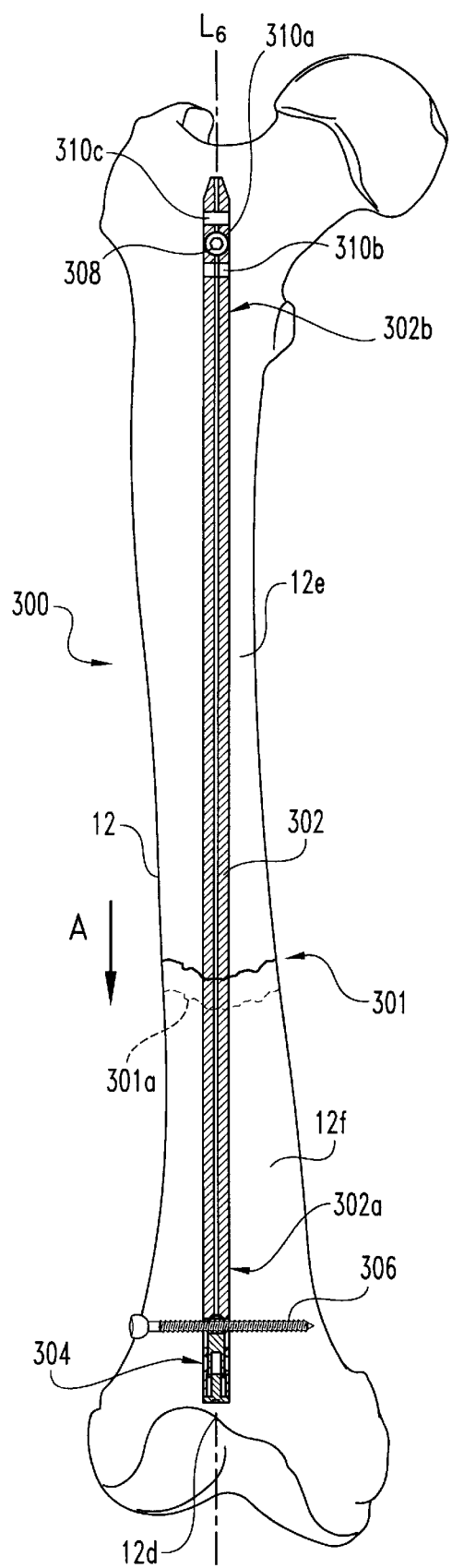
FIG. 15 is a side view, partly in section, of another rod system of the present invention for performing distraction of a bone fracture.

Referring now to FIG. 15, intramedullary system 300 according to still another embodiment of the present invention is illustrated; where reference numerals of previously described embodiments refer to like features. System 300 is shown implanted in femur 12 and includes elongated intramedullary nail 302, positioning device 304, bone engaging member 306 and locking bone screw 308. Femur 12 includes a fracture site 301, separating femur 12 into two portions 12f, 12e. Fracture site 301 is shown in a compressed state (i.e., portions 12f, 12e are being pushed together). Although system 300 is shown implanted in femur 12, system 300 could also be used in conjunction with other bones such as the tibia, humerus, radius, ulna and fibula to name a few. Additionally, the same components of system 300 can be used to treat either a left or right femur by simply rotating nail 302 180 degrees relative to axis $L_6$. Although FIG. 15 illustrates nail 302 implanted within femur 12 in a retrograde direction, it is understood that system 300 could also be implanted with nail 302 in an antegrade direction.

Figure 16:
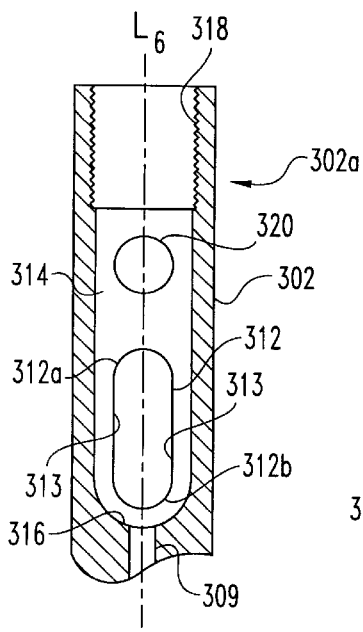
FIG. 16 is a partial, sectional side view of the proximal end portion of the rod of FIG. 15.

FIGS. 15 and 16 show various structural details of nail 302. It should be understood that nail 302 can take on a number of configurations, including that of nail 14 illustrated and described above. However, in a preferred embodiment, nail 302 is configured as described below. Nail 302 includes a proximal end portion 302a and a distal end portion 302b. Nail 302 also defines a longitudinal axis $L_6$ running along the length of nail 302 between proximal end portion 302a and distal end portion 302b. Proximal end portion 302a preferably has a diameter of about 11–12 millimeters for an adult human femur application. The diameter of the remainder of nail 302 can be varied depending upon the requirements of the fixation procedure and the surgeon's preference. While nail 302 has a generally circular cross section, other suitable shapes are also contemplated as would occur to one skilled in the art.

Nail 302 defines a passage 309 extending therethrough along axis $L_6$ line to allow for the optional use of a guide wire (not shown) to aid in the insertion of nail 302 in femur 12. Distal end portion 302b defines parallel transverse bores 310b, 310c, each sized to receive locking bone screw 308. Distal end portion 302b also defines transverse bore 310a, aligned generally perpendicular to transverse bores 310b, 310c and also sized to receive locking bone screw 308.

Proximal end portion 302a defines an elongated, longitudinal opening 312 bounded by side walls 313 and sized to receive bone engaging member 306 therein. Opening 312 laterally extends through nail 302 and is elongated in the direction of longitudinal axis $L_6$. Opening 312 has a first end portion 312a and an opposing second end portion 312b. Proximal end portion 302a of nail 302 also defines a longitudinal passage 314 extending generally along axis $L_6$ and having a generally circular cross-section. Longitudinal passage 314 intersects opening 312 and terminates in a generally concave bottom surface 316. A threaded portion 318 is defined about a portion of longitudinal passage 314. Proximal end portion 302a also defines a transverse bore 320 extending through nail 302 generally perpendicular to axis $L_6$ and aligned with opening 312. Bore 320 is sized to receive bone engaging member 306 therein.

Figure 17:
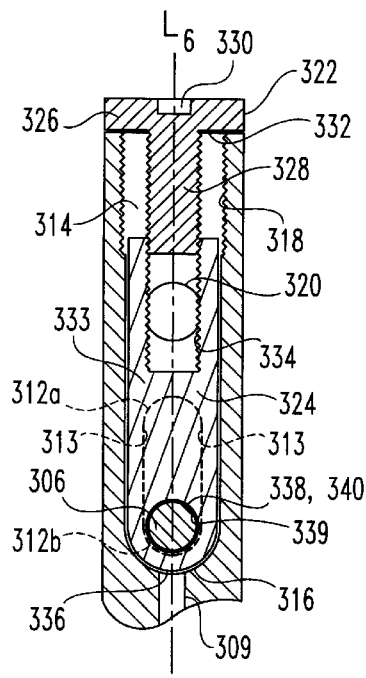
FIG. 17 is a partial, sectional side view of the proximal end portion of the system of FIG. 15, illustrating a first operational position.

Referring to FIG. 17, therein is shown nail 302, positioning device 304 and bone engaging member 306 as assembled within system 300. Positioning device 304 is shown positioned within longitudinal passage 314 and includes a first portion 322 and a second portion 324. First portion 322 includes a head 326 and a threaded stem 328 extending therefrom generally along longitudinal axis $L_6$. Head 326 is substantially circular and has an outer diameter generally corresponding to the outer diameter of nail 302. Head 326 also includes a hex recess 330 for receiving a driving tool (not shown), such as an Allen wrench. The diameter of threaded stem 328 is less than the diameter of head 326, thereby defining an annular shoulder 332.

Second portion 324 defines a generally circular, elongated body 333 having a diameter slightly less than the diameter of longitudinal passage 314. Second portion 324 also defines an internally threaded portion 334 extending generally along longitudinal axis $L_6$ and configured to threadedly engage threaded stem 328 of first portion 322. Threaded portion 334 has a depth slightly greater than the length of threaded stem 328. The end of second portion 324 opposite threaded portion 334 terminates into a generally convex outer surface 336 that substantially corresponds to concave bottom surface 316 of longitudinal passage 314. Second portion 324 also defines a transverse opening 338 extending therethrough generally perpendicular to longitudinal axis $L_6$. Opening 338 is bounded by inner surface 339 and is sized to receive bone engaging member 306 therein.

FIG. 17 illustrates a first operational position of system 300. Positioning device 304 (including first and second portions 322, 324) is shown inserted within longitudinal passage 314 of nail 302. Opening 338 of second portion 324 is positioned adjacent second end portion 312b of opening 312 and generally aligned with opening 312 to define a passageway 340. Bone engaging member 306 is shown inserted through passageway 340. Threaded stem 328 of first portion 322 is partially threadedly engaged within threaded portion 334 of second portion 324. First portion 322 can be rotated by placing a driving tool (not shown) within hex recess 330 and turning in a clockwise or counterclockwise direction as appropriate. Second portion 324 is prevented from rotating in correspondence with first portion 322 because of engagement between bone engaging member 306 against sidewalls 313 of opening 312. In one embodiment, threaded stem 328 and threaded portion 334 each have right-handed threads. In this embodiment, as first portion 322 is rotated in a clockwise direction, shoulder 332 of head 326 bears against nail 302, and second portion 324 correspondingly moves toward first portion 322 generally along longitudinal axis $L_6$. As the position of second portion 324 is adjusted along axis $L_6$, inner surface 339 of opening 338 bears against bone engaging member 306 and correspondingly adjusts the position of bone engaging member 306 along the length of opening 312.

Figure 18:
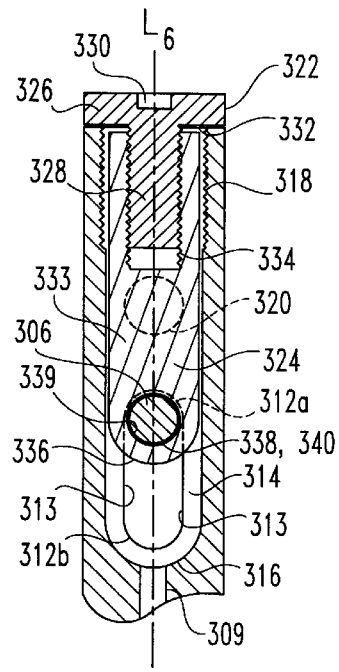
FIG. 18 is a partial, sectional side view of the proximal end portion of the system of FIG. 15, illustrating a second operational position.

FIG. 18 illustrates a second operational position of system 300 in which first portion 322 is rotated in a clockwise direction until bone engaging member 306 is positioned adjacent first end portion 312a of opening 312. It should be understood, however, that bone engaging member 306 can be variably positioned anywhere along the length of opening 312. It should further be understood that the terms "first operational position" and "second operational position" are not necessarily indicative of the initial position and adjusted position of bone engaging member 306. For example, bone engaging member 306 could originate in a position adjacent first end portion 312a and be variably positioned anywhere along the length of opening 312.

In other embodiments of system 300, nail 302 defines a keyway extending along the length of longitudinal passage 314 generally parallel with axis $L_6$. Additionally, second portion 324 defines a key along its length which generally corresponds to the keyway defined in nail 302. Preferably, the key is radially positioned so that when it is slidably received within the keyway, opening 338 of second portion 324 will correspondingly align with opening 312 of nail 302. Alternatively, the key could be defined along the length of second portion 324 and, correspondingly, the keyway could be defined along the length of longitudinal passage 314 of nail 302.

Having described selected structural and operational features of nail 302 and positioning device 304, the operational characteristics of system 300 will now be described in further detail. Referring back to FIG. 15, nail 302 is shown implanted in femur 12. Distal end 302b of nail 302 is anchored to portion 12e of femur 12 by inserting locking bone screw 308 into portion 12e and through transverse bore 310a (not shown) of nail 302. Proximal end 302a of nail 302 is anchored to portion 12f of femur 12 by inserting bone engaging member 306 into portion 12f and through passageway 340 (defined by aligning opening 338 with opening 312). Preferably, bone engaging member 306 is initially positioned adjacent or near second end portion 312b of opening 312. As first portion 322 of positioning device 304 is rotated in a clockwise direction, bone engaging member 306 is correspondingly repositioned along the length of opening 312, and more specifically is transferred toward first end portion 312a. Because bone engaging member 306 is anchored to portion 12f of femur 12, portion 12f is correspondingly moved in the direction of arrow "A", while portion 12e of femur 12 remains stationery, securely anchored to distal end 302b of nail 302. Thus, portion 12f of femur 12 is repositioned away from portion 12e, thereby distracting fracture site 301.

One preferred procedure for implanting system 300 within femur 12 includes forming a longitudinal hole along the medullary canal from a point generally central to the distal end portion 12d of femur 12. Preferably this hole is formed by drilling sized to receive nail 302 therethrough. Positioning device 304 is inserted in longitudinal passage 314 of nail 302 and nail 302 is inserted through the longitudinal hole and into the medullary canal. It should be understood that positioning device 304 could alternatively be inserted in longitudinal passage 314 after nail 302 has been implanted in femur 12. A first passage is formed through femur 12 transverse to the medullary canal and generally aligned with transverse bore 310a (not shown) formed in distal portion 302b of nail 302. A second passage is formed through femur 12 transverse to the medullary canal and generally aligned with passageway 340. Preferably, these transverse passages are formed by drilling. Locking bone screw 308 is threaded into the first passage, passing through transverse bore 310a. Bone engaging member 306 is threaded into the second passage, passing through passageway 340. At this point, fracture site 301 can be distracted by following the operational procedure described above. Dashed line 301a of FIG. 15 corresponds to the position of the fractured end of portion 12f after distraction in accordance with one embodiment of the present invention.

Figure 19:
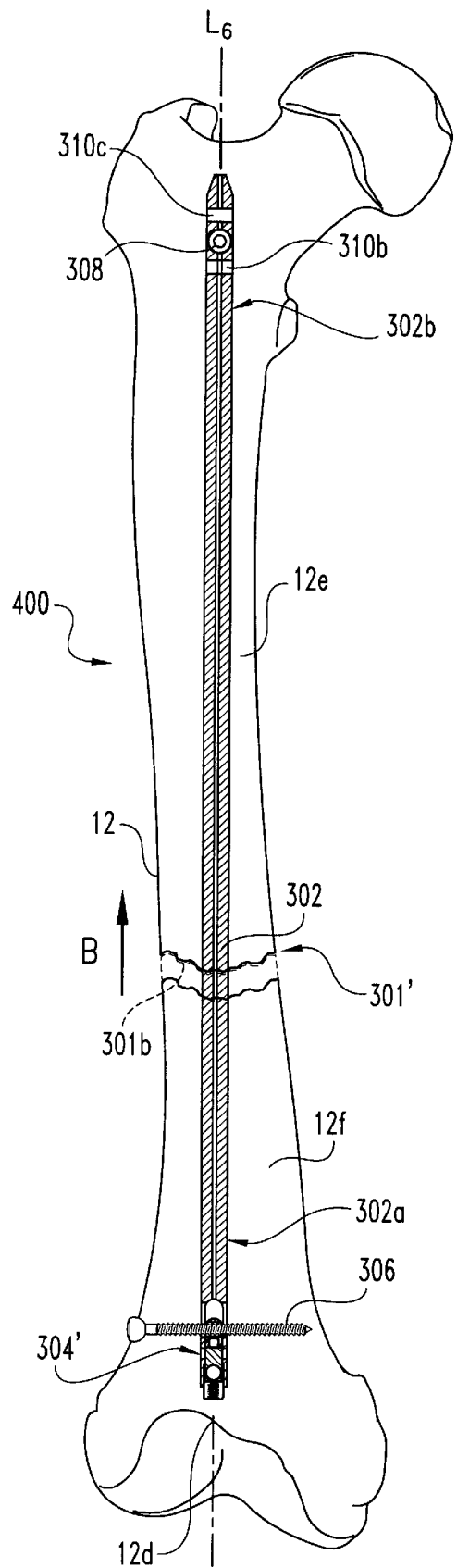
FIG. 19 is a side view, partly in section, of an additional intramedullary rod system of the present invention for performing compression of a bone fracture.

Referring now to FIG. 19, intramedullary system 400 according to yet another embodiment of the present invention is illustrated; where like reference numerals of previously described embodiments refer to like features. System 400 is shown implanted in femur 12 and includes elongated intramedullary nail 302, positioning device 304', bone engaging member 306 and locking bone screw 308. Femur 12 includes a fracture site 301', separating femur 12 into two portions 12f, 12e. Fracture site 301' is shown in a distracted state (i.e., portion 12a, 12b are spaced apart relative to one another). Although system 400 is shown implanted in femur 12, system 400 could also be used in conjunction with other bones as would occur to one skilled in the art, including the tibia, humerus, radius, ulna and fibula, to name a few. Additionally, the same components of system 400 can be used to treat either a left or right femur by simply rotating nail 302 180 degrees relative to axis $L_6$. Although FIG. 19 illustrates nail 302 implanted within femur 12 in a retrograde direction, it is understood system 400 may also be implanted with nail 302 in an antegrade direction.

Figure 20:
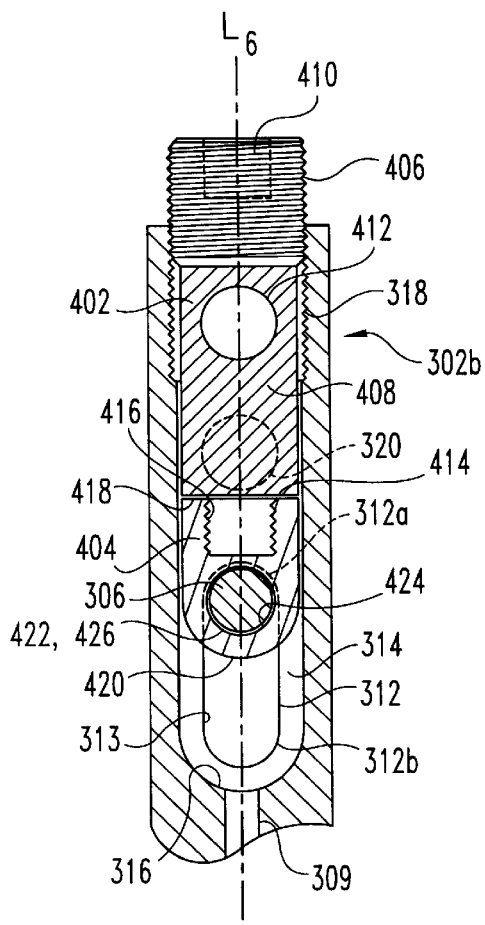
FIG. 20 is a partial, sectional side view of the proximal end portion of the system of FIG. 19, illustrating a first operational position.

Referring to FIG. 20, therein is shown nail 302, positioning member 304' and bone engaging member 306 as assembled within system 400. Positioning member 304' is shown positioned within longitudinal passage 314 and includes a first portion 402 and a second portion 404. First portion 402 includes a threaded upper portion 406 and an elongated lower portion 408 extending therefrom along longitudinal axis $L_6$. Upper portion 406 is configured to threadedly engage threaded portion 318 of longitudinal passage 314. Upper portion 406 also includes a hex recess 410 for receiving a driving tool (not shown), such as an Allen wrench. Lower portion 408 has a generally circular body having an outer diameter slightly less than the diameter of longitudinal passage 314. A transverse passage 412 extends through lower portion 408 and is aligned generally perpendicular to axis $L_6$. The end of lower portion 408 opposite its threaded portion terminates in a generally flat surface 414.

Second portion 404 has a circular body having an outer diameter generally corresponding to the outer diameter of lower portion 408 of first portion 402. Second portion 404 defines an internally threaded portion 416 extending generally along axis $L_6$ for engaging insertion instrumentation (not shown). One end of second portion 404 defines a generally flat surface 418, corresponding to surface 414 of lower portion 408. The opposing end of second portion 404 terminates in a generally convex outer surface 420 substantially corresponding to concave bottom surface 316 of longitudinal passage 314. Second portion 404 also defines a transverse opening 422 extending therethrough generally perpendicular to axis $L_6$. Opening 422 is bound by inner surface 424 and is sized to receive bone engaging member 306 therein.

FIG. 20 illustrates a first operational position of system 400. Positioning device 304' (including first and second portions 402, 404) is shown inserted within longitudinal passage 314 of nail 302. Opening 422 of second portion 404 is positioned adjacent first end portion 312a of opening 312 and generally aligned with opening 312 to define a passageway 426. Bone engaging member 306 is shown inserted through passageway 426. Upper portion 406 of first portion 402 is partially threadedly engaged within threaded portion 318 of longitudinal passage 314. First portion 402 can be rotated by placing a driving tool (not shown) within hex recess 410 and turning first portion 402 in a clockwise or counterclockwise direction. In one embodiment, threaded upper portion 406 and threaded portion 318 each have right-handed threads. In this embodiment, as first portion 402 is rotated in a clockwise direction, it will be advanced through longitudinal passage 314 generally along axis $L_6$. As first portion 402 is advanced, surface 414 will engage surface 418 of second portion 404, thereby correspondingly advancing second portion 404 through longitudinal passage 314 generally along axis $L_6$. As the position of second portion 404 is adjusted along axis $L_6$, inner surface 424 of opening 422 bears against bone engaging member 306 and correspondingly adjusts the position of bone engaging member 306 along the length of opening 312.

Figure 21:
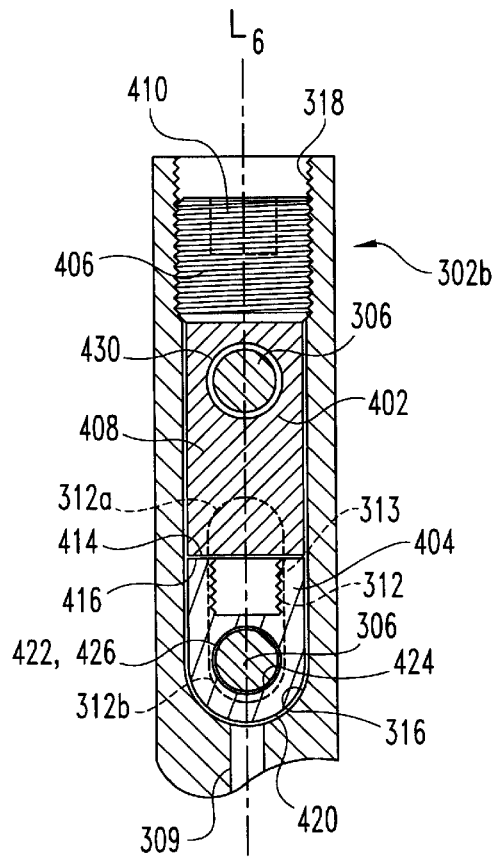
FIG. 21 is a partial, sectional side view of the proximal end portion of the system of FIG. 19, illustrating a second operational position.

FIG. 21 illustrates a second operational position of system 400 in which first portion 402 is rotated in a clockwise direction until bone engaging member 306 is positioned adjacent second end portion 312b of opening 312. It should be understood, however, that bone engaging member 306 can be variably positioned anywhere along the length of opening 312. It should further be understood that the terms "first operational position" and "second operational position" are not necessarily indicative of the initial position and adjusted position of bone engaging member 306. For example, bone engaging member 306 could originate in a position adjacent second end portion 312b and be variably positioned anywhere along the length of opening 312.

When bone engaging member 306 is positioned adjacent second end portion 312b of opening 312, transverse passage 412 of upper portion 406 will become aligned with transverse bore 320 of nail 302, thereby defining a passageway 430. A second bone engaging member 306 can then be inserted through passageway 430 to prevent further rotational movement of first portion 402 relative to nail 302. However, if transverse passage 412 and transverse bore 320 cannot be aligned to form passageway 430, a second bone engaging member 306 cannot be used. In this case, in order to prevent first portion 402 from rotating and migrating relative to nail 302, a locking set screw can be threadedly advanced along threaded portion 318 of nail 302 until it tightly engages upper portion 406.

Having described selected structural and operational features of positioning device 304', the operational characteristics of system 400 will now be described in further detail. Referring back to FIG. 19, nail 302 is shown implanted in femur 12 and is anchored to portions 12a and 12b in substantially the same manner as described above in system 300. Preferably, bone engaging member 306 is initially positioned adjacent or near first end portion 312a of opening 312. As first portion 402 of positioning device 304' is rotated in a clockwise direction, bone engaging member 306 is correspondingly repositioned along the length of opening 312, and more specifically is transferred toward second end portion 312b of opening 312. Because bone engaging member 306 is anchored to portion 12f of femur 12, portion 12f is correspondingly moved in the direction of arrow "B", while portion 12e of femur 12 remains stationary, securely anchored to distal end 302b of nail 302. Thus, portion 12f of femur 12 is repositioned toward portion 12e, thereby compressing fracture site 301'. Dashed line 301b of FIG. 19 corresponds to the fractured end of portion 12f after compression in accordance with one embodiment of the present invention.

One preferred procedure for implanting system 400 within femur 12 is substantially identical to the procedure for implanting system 300, except a compression operation as described above is performed instead of the distraction operation as described in connection with system 300.

The components of systems 10, 100, 165, 195, 200, 300 and 400 maybe fabricated from any suitably strong, biocompatible material such as stainless steel, titanium, chrome-cobalt, or any other material which would occur to those skilled in the art.

While the invention has been illustrated and described in detail in the drawings and foregoing discussion, the same is to be considered as illustrative and not restrictive in character, it being understood that only the preferred embodiments have been shown and described and that all changes and modifications that come within the spirit of the invention are desired to be protected.

What is claimed is:

1. A system for treating bone fractures, the system comprising:
   an intramedullary nail defining an opening, said opening having an upper surface and a lower surface;
   a transverse member including a bone engaging portion and a connection portion, said connection portion defining a thru-hole, said nail being sized to pass through said thru-hole; and
   a pin selectively attached to said transverse member and operable to rigidly assemble said transverse member to said nail when said nail passes through said thru-hole and said pin is received within said opening.

2. The system of claim 1 wherein said transverse member defines a passage intersecting said through-hole.

3. The system of claim 2 wherein said passage includes a threaded portion, said pin includes a leading portion and a trailing portion, said leading portion has an elongated section configured to be slidably received within said opening, said trailing portion has external threads to engage said threaded portion to advance said pin through said passage.

4. The system of claim 1 wherein said pin includes an engaging surface configured to engage said nail and clamp said nail against said transverse member.

5. The system of claim 1 wherein said pin includes a leading portion and a trailing portion, one of said leading portion and said trailing portion includes a ball member and another of said leading portion and said trailing portion includes a socket member, said ball and socket members cooperating to permit angular variation between said leading portion and said trailing portion.

6. The system of claim 5 wherein said nail defines a first longitudinal axis and said opening defines a generally straight pathway positioned at about 135 degrees relative to said first longitudinal axis, said transverse member defines a second longitudinal axis and said through-hole is positioned within a range of about 130 to 145 degrees relative to said second longitudinal axis.

7. The system of claim 1 wherein said connection portion is adapted to slidably receive said bone engaging portion.

8. The system of claim 7 wherein said bone engaging portion includes a keeper, said connection portion includes an inner retaining lip, said keeper co-acting with said retaining lip to provisionally maintain said bone engaging portion and said connection portion in sliding engagement.

9. The system of claim 1 further comprising a locking mechanism positioned adjacent said pin to prevent movement of said pin relative to said transverse member.

10. The system of claim 1 wherein said nail defines a longitudinal axis and includes a longitudinal passageway extending at least partially therethrough and intersecting said opening, a portion of said longitudinal passageway being threaded to engage a set screw, said set screw including a stem portion adapted to be slidably received within said longitudinal passageway to lockingly engage said pin.

11. The system of claim 1 wherein said nail defines a longitudinal axis, said lower surface of said opening defines a first angled portion to engage said pin in an abutting relationship with said pin oriented at a first oblique angle relative to said longitudinal axis.

12. The system of claim 11 wherein said upper surface of said opening defines a second angled portion generally opposite said first angled portion to engage said pin when said pin is oriented at said first oblique angle.

13. The system of claim 12 wherein said lower surface defines a third angled portion to engage said pin in another abutting relationship with said pin oriented at a second oblique angle relative to said longitudinal axis.

14. The system of claim 13 wherein said upper surface defines a fourth angled portion generally opposite said third angled portion to engage said pin when said pin is oriented at said second oblique angle.

15. The system of claim 14 wherein said first and second oblique angles are each about 135 degrees.

16. The system of claim 14 wherein said opening extends through said nail, and wherein said first and third angled portions define a first apex and said second and fourth angled portions define a second apex opposite said first apex.

17. A device for treating bone fractures, the device comprising:
    an intramedullary nail defining an opening, said opening having an upper surface and a lower surface;
    a transverse member including means for engaging bone, said transverse member defining a thru-hole, said nail being sized to pass through said thru-hole; and
    means for locking said transverse member in position relative to said nail, said locking means including a pin sized to pass through said opening and rigidly assemble said transverse member to said nail.

18. The device of claim 17 wherein said transverse member defines a longitudinal axis and includes means for permitting free movement of said engaging means along said longitudinal axis of said transverse member.

19. The device of claim 18 wherein said transverse member includes means for provisionally maintaining said engaging means and said transverse member in sliding engagement.

20. The device of claim 17 wherein said locking means includes a means for allowing angular variation between said locking means and said transverse member.

21. The system of claim 17 wherein said opening extends through said nail.

22. A method of treating a bone fracture, the method comprising:
    forming a first hole in a femur transverse to the medullary canal;
    introducing a transverse bone engaging member through the first hole, the bone engaging member including a thru-hole, the thru-hole being positioned adjacent the medullary canal;
    forming a second hole into the medullary canal;
    inserting an intramedullary nail into the medullary canal through the second hole, the nail passing through the thru-hole of the bone engaging member, the nail including an opening positioned adjacent the bone engaging member, the opening having an upper surface and a lower surface; and
    rigidly assembling the bone engaging member and the nail by passing a pin selectively coupled to the bone engaging member into the opening of the nail.

23. The method of claim 22 including adjusting the angular position of the pin relative to the bone engaging member.

24. The method of claim 22 wherein the assembling includes threading the pin into a passage defined by the bone engaging member, the passage intersecting the thru-hole.

25. The method of claim 22 wherein the upper and lower surfaces are angled to define a first apex opposite a second apex.

26. The method of claim 22 wherein the introducing includes threading at least a portion of the bone engaging member into bone.

\* \* \* \* \*